United States Patent
Malecha et al.

(10) Patent No.: US 6,172,256 B1
(45) Date of Patent: Jan. 9, 2001

(54) CHIRAL-β-AMINO ACID COMPOUNDS AND DERIVATIVES THEREOF

(75) Inventors: James W. Malecha, Libertyville; Thomas P. Fraher, Chicago, both of IL (US)

(73) Assignee: G.D. Searle & Co., Chicago, IL (US)

( * ) Notice: Under 35 U.S.C. 154(b), the term of this patent shall be extended for 0 days.

(21) Appl. No.: 09/261,647

(22) Filed: Mar. 3, 1999

Related U.S. Application Data

(63) Continuation-in-part of application No. 09/034,270, filed on Mar. 4, 1998, now abandoned.

(51) Int. Cl.[7] .................................................. C07C 229/00
(52) U.S. Cl. .................................................................. 560/38
(58) Field of Search ..................................................... 560/38

(56) References Cited

U.S. PATENT DOCUMENTS

| | | | |
|---|---|---|---|
| 5,753,230 | * | 5/1998 | Brooks .............................. 424/158.1 |
| 5,766,591 | * | 6/1998 | Brooks et al. ..................... 424/184.1 |

FOREIGN PATENT DOCUMENTS

| | | |
|---|---|---|
| WO97 08145 | 3/1997 | (WO) . |
| WO 9952896 | * 10/1999 | (WO) . |

OTHER PUBLICATIONS

Pommier, Y. et al., "HIV–1 Integrase as target for antiviral drugs," Antiviral Chemistry & Chemotherapy, vol. 8 (No. 6), pp. 463–483, 1997.*

Nicklaus, M.C. et al., "HIV–1 Integrase Pharmacophore: Discovery of Inhibitors through Three–Dimensional Database Searching," J. Med. Chem, 7th ed., American Chemical Society, V. 40, pp. 920–929, 1997.*

Hong, H. et al., "Discovery of HIV–1 Integrase Inhibitors by Pharmacophore Searching," J. Med. Chem, American Chemical Society, V. 40, pp. 930–936, 1997.*

Fields, Gregg B., "Integrins: cell adhesion molecules in cancer," Exp. Opin. Ther. Patents, Ashley Publicaations, Ltd., vol. 8 (No. 6), pp. 633–644, 1998.*

* cited by examiner

Primary Examiner—Gary Geist
Assistant Examiner—D Khare
(74) Attorney, Agent, or Firm—Cynthia S. Kovacevic

(57) ABSTRACT

The present invention is directed to a method for the preparation of a chiral β-amino ester of the formula

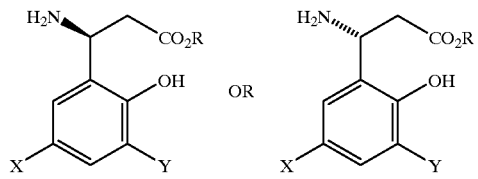

wherein R is lower alkyl; and X and Y are the same or different Cl, Br or I.

6 Claims, No Drawings

CHIRAL-β-AMINO ACID COMPOUNDS AND DERIVATIVES THEREOF

The present application is a CIP of and claims priority from U.S. patent application Ser. No. 09/034,270 filed Mar. 4, 1998, now abandoned.

FIELD OF THE INVENTION

The present invention relates to a chiral separation method useful for preparing chiral β-amino esters which are useful for the preparation of $\alpha_v\beta_3$ integrin antagonists. Such $\alpha_v\beta_3$ integrin antagonists are useful in pharmaceutical compositions and in methods for treating conditions mediated by $\alpha_v\beta_3$, by inhibiting or antagonizing integrins.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked α and β polypeptide subunits. Currently eleven different α subunits have been identified and six different β subunits have been identified. The various α subunits can combine with various β subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis, Paget's disease, humoral hypercalcemia of malignancy, angiogenesis, including tumor angiogenesis, retinopathy, including macular degeneration, arthritis, including rheumatoid arthritis, periodontal disease, psoriasis and smooth muscle cell migration (e.g. restenosis). Additionally, it has been found that such agents would be useful as antivirals, antifungals and antimicrobials. Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy and macular degeneration (Adonis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic targets for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (a loss of bone), which leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

U.S. Ser. No. 09/034,270 discloses compounds of the following general formula

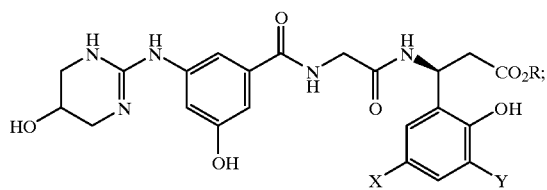

wherein X and Y are the same or different halo group; R is H or alkyl; and pharmaceutically acceptable salts thereof. Such compounds find use as $\alpha_v\beta_3$ integrin antagonists.

More specifically, U.S. Ser. No. 09/034,270 discloses the following compounds:

(I)
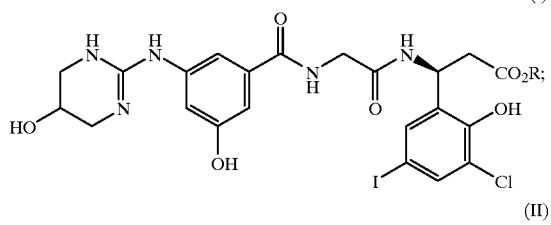

(II)
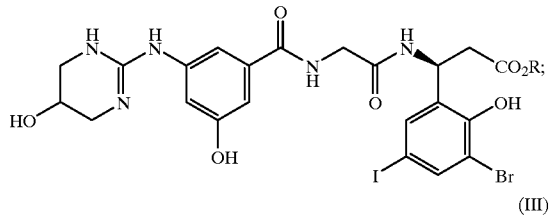

(III)
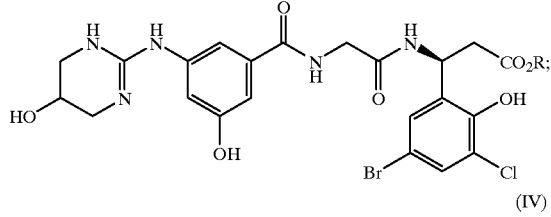

(IV)
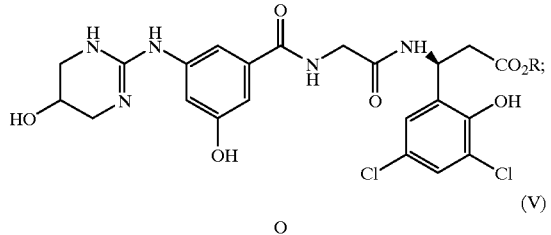

(V)
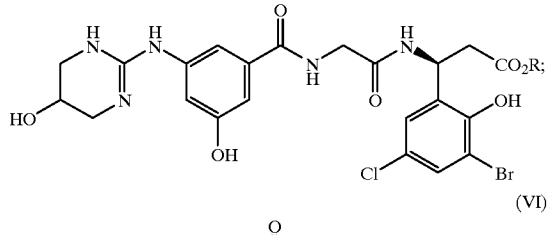

(VI)
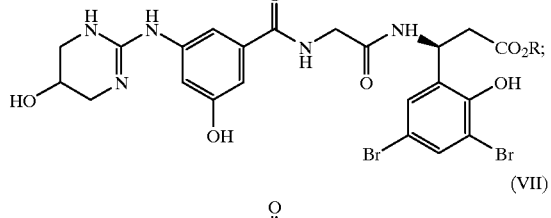

(VII)
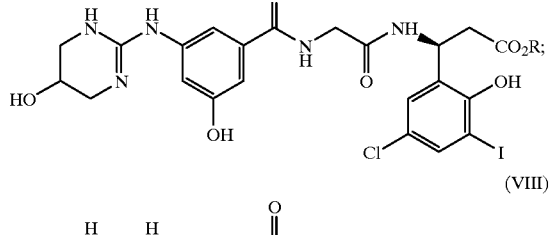

(VIII)
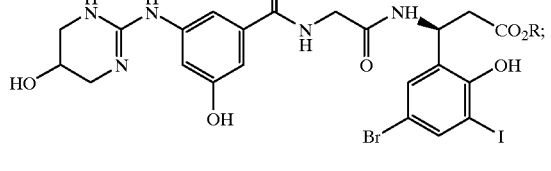

and (IX)
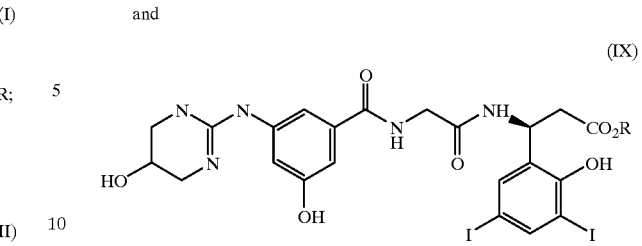

wherein R is H or alkyl; or pharmaceutically acceptable salts thereof. Each of these compounds contains a chiral β-amino acid/ester moiety which is substituted by halogens. In order to prepare such $\alpha_v\beta_3$ antagonists, it is therefore useful to have methodology to efficiently prepare a chiral β-amino acid/ester.

Chiral chromatography to separate enantiorners is known [Péter et al., Analytica Chimica Acta, 352 (1997) 335–356] and is a possible method for preparing such chiral compounds. The present invention provides a novel method for preparation of chiral β amino esters which are useful in the preparation of $\alpha_v\beta$ antagonists described above.

SUMMARY OF THE INVENTION

The present invention relates to a method for the preparation of chiral β-amino esters of the formula.

(I)
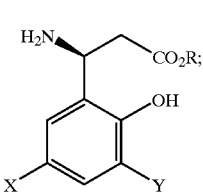

comprising protecting the amino group of a racemic amino acid of the formula (II)
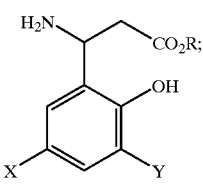

with CBZ to form a protected amino acid of the formula (III)
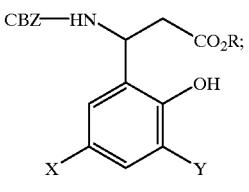

subjecting the protected amino acid of the formula III to chiral chromatography to obtain a protected amino acid of the formula

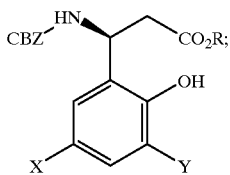

(IV)

deprotecting the amino acid of the formula IV by reacting said amino acid with trimethylsilyl iodide in dichloromethane; and isolating the amino acid of the formula I.

DETAILED DESCRIPTION

The present invention relates to a method of preparation of chiral β-amino esters of the formula

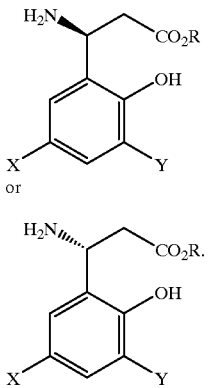

The invention comprises a process starting from the racemic β-amino ester. The first step comprises the step of protecting the amino group of the racemic β-amino ester of the formula

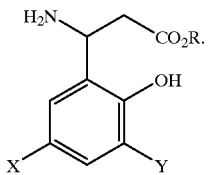

(I)

Preferably the present invention provides for protection of the β-amino ester with CBZ. The protection step results in a protected racemic β-amino ester of the formula

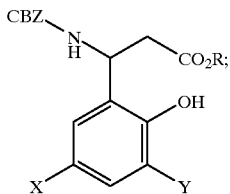

(II)

and allows for the chiral separation of the (R) and (S) β-amino esters from the racemic mixture.

A chiral separation is performed on the compound of formula II, using methodology known to those skilled in the art to yield each enantiomer as the CBZ-β-amino ester of the formula.

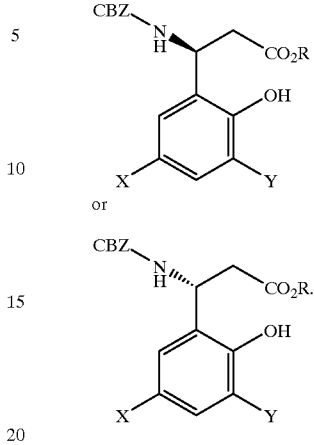

The CBZ protecting group is then removed to give a β-amino ester as a single isomer. Although standard, well known, established methods exist for removing protecting groups, including the CBZ group, such deprotecting methodologies resulted in loss of the aromatic halogens. Due to the unique structure of the β-amino acids needed for preparation of the integrin antagonists described above, the deprotection step employing standard deprotection methodologies was accompanied by loss of the aromatic halogens. The loss of such halogens did not result in the chiral β-amino esters needed for the preparation of the peptidomimetic $\alpha_v\beta_3$ integrin antagonists described above. After much investigation it was found that treating the protected β-amino esters with trimethylsilyl iodide in dichloromethane could be used to deprotect the amines while leaving the aromatic halogens intact.

The preferred conditions are described in Example K of this application and in Example K of U.S. Ser. No. 09/034, 270 and also in Example Q, Step I, Example R and Example S of the present application. Such deprotection results in β-amino esters of the following formulae:

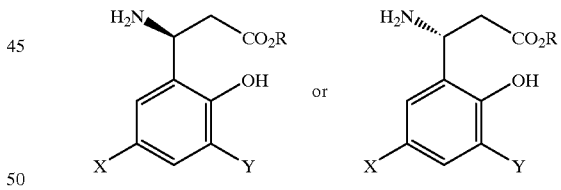

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the term "halo" or "halogen" refers to bromo, chloro, or iodo.

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR=proton nuclear magnetic resonance
AcOH=acetic acid
Ar=argon
BOC=t-Butoxycarbonyl
CBZ=

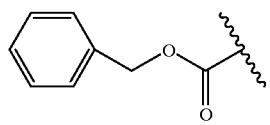

$CH_3CN$=acetonitrile
CHN analysis=carbon/hydrogen/nitrogen elemental analysis
CHNCl analysis=carbon/hydrogen/nitrocgen/chlorine elemental analysis
CHNS analysis=carbon/hydrogen/nitro(gen/sulfur elemental analysis
DI water=deionized water
DMA=N,N-dimethylacetamide
DMAP=4-(N,N-dimethylamino)pyridine
DMF=N,N-dimethylformamide
EDCl=1-(3-dimethylaminopropyl)-3-ethylcarbodiimide hydrochloride
EtOAc=ethyl acetate
EtOH=ethanol
FAB MS=fast atom bombardment mass spectroscopy
g=gram(s)
HOBT=1-hydroxybenzotriazole hydrate
HPLC=high performance liquid chromatography
IBCF=isobutylchloroformate
KSCN=potassium thiocyanate
L=liter
LiOH=lithium hydroxide
MEM=methoxyethoxymethyl
MEMCl=methoxyethoxymethyl chloride
MeOH=methanol
mg=milligram
$MgSO_4$=magnesium sulfate
ml=milliliter
mL=milliliter
MS=mass spectroscopy
MTBE=methyl tert-butyl ether
$N_2$=nitrogen
$NaHCO_3$=sodium bicarbonate
NaOH=sodium hydroxide
$Na_2SO_4$=sodium sulfate
NMM=N-methylmorpholine
NMP=N-methyl pyrrolidinone NMR=nuclear magnetic resonance
$P_2O_5$=phosphorous pentoxide
PTSA=para-toluenesulfonic acid
RPHPLC=reverse phase high performance liquid chromatography
RT=room temperature
TFA=trifluoroacetic acid
THF=tetrahydrofuran
TMS=trimethylsilyl
Δ=heating the reaction mixture The compounds described herein can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound described above with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, tartrate salts and the like. All of the pharmacologically acceptable salts may be prepared by conventional means. (See Berge et al., *J Pharm. Sci.*, 66(1), 1–19 (1977) for additional examples of pharmaceutically acceptable salts.)

For the selective inhibition or antagonism of $\alpha_v\beta_3$ integrins, the $\alpha_v\beta_3$ integrin antagonists compounds described herein may be may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The $\alpha_v\beta_3$ integrin antagonists compounds described herein are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

The $\alpha_v\beta_3$ integrin antagonist described herein provide a method of treating conditions mediated by selectively inhibiting or antagonizing the $\alpha_v\beta_3$ cell surface receptor which method comprises administering a therapeutically effective amount of a described compound selected from the class of compounds described above, wherein one or more compounds is administered in association with one or more non-toxic, pharmaceutically acceptable carriers and/or diluents and/or adjuvants (collectively referred to herein as "carrier" materials) and if desired other active ingredients. Administration of an $\alpha_v\beta_3$ integrin antagonist provides a method for inhibition of the $\alpha_v\beta_3$ cell surface receptor. Most preferably administration of the $\alpha_v\beta_3$ antagonist provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy and macular degeneration, inhibiting arthritis, psoriasis and periodontal disease, and inhibiting smooth muscle cell migration including restenosis.

The present invention provides a method for preparing the chiral β-amino esters useful for the preparation of the $\alpha_v\beta_3$ integrin antagonists described herein. The method provides for preparation of the chiral β-amino esters from the racemic starting material. The method offers advantages over a chiral synthesis in that both isomers of the β-amino ester can be prepared in a single sequence and the method starts with the racemic material as opposed to needing a single enantiomer starting material.

Based upon standard laboratory experimental techniques and procedures well known and appreciated by those skilled in the art, as well as comparisons with compounds of known usefulness, the $\alpha_v\beta_3$ antagonist compounds described above can be used in the treatment of patients suffering from the above pathological conditions. One skilled in the art will recognize that selection of the most appropriate $\alpha_v\beta_3$ antagonist compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound described above which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially control led to some extent.

The general synthetic sequences for preparing the $\alpha_v\beta_3$ integrin antagonists described above, and starting materials useful for preparing the β-amino acid esters are outlined in Schemes I–III. The Schemes and Examples described hereinafter describe 1) the preparation of the racemic starting materials used in the present invention; 2) the details of the chiral separation methodology of the present invention; 3) the alternative chiral synthetic methodology used to prepare a single enantiomer of the β-amino esters; and 4) the use of the β-amino esters prepared by the chiral separation methodology in preparing $\alpha_v\beta_3$ integrin antagonists. Both an explanation of, and the actual procedures for, the various aspects of the present invention are described where appropriate.

The following Schemes and Examples are intended to be merely illustrative of the present invention, and not limiting thereof in either scope or spirit. Those with skill in the art will readily understand that known variations of the conditions and processes described in the Schemes and Examples can be used in the present invention.

Unless otherwise indicated all starting materials and equipment employed were commercially available.

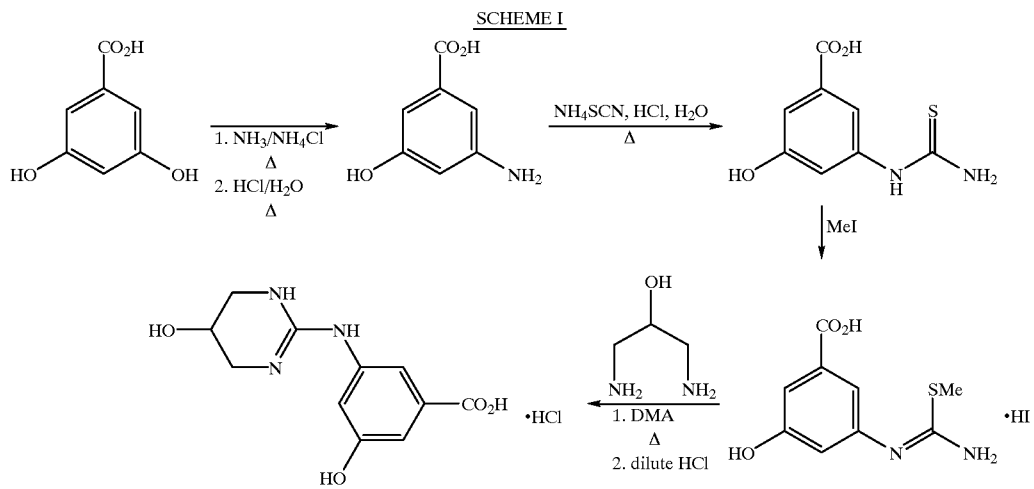

Scheme I illustrates methodology useful for preparing the tetrahydropyrimidinobenzoic acid portion of the $\alpha_v\beta_3$ integrin antagonists described herein which can be coupled to a gly-β-amino acid ester. Briefly, in Scheme I, 3,5-dihydroxybenzoic acid is converted to 3-amino-5-hydroxybenzoic acid using the procedure described in *Austr. J. Chem.*, 34 (6), 1319–24 (1981). The product is reacted with ammonium thiocyanate in hot dilute hydrochloric acid to give 3-thiourea-5-hydroxybenzoic acid after normal workup. This thiourea intermediate is converted to the S-methyl derivative by reaction with methyl iodide in ethanol at reflux. 1,3-diamino-2-hydroxypropane is reacted with this resulting intermediate in hot DMA. Upon cooling precipitate forms and the zwitterioric product is isolated by filtration. The HCl salt may be obtained by lyophilizing from dilute hydrochloric acid. Alternatively, the product may be isolated from the original reaction mixture by removing volatiles and concentrating. The resulting product is taken up in water and pH adjusted to about 5–7 where zwitterionic product precipitates and is isolated by filtration. The HCl salt may be obtained as previously stated or by simply dissolving in dilute hydrochloric acid and concentrating to a solid and drying.

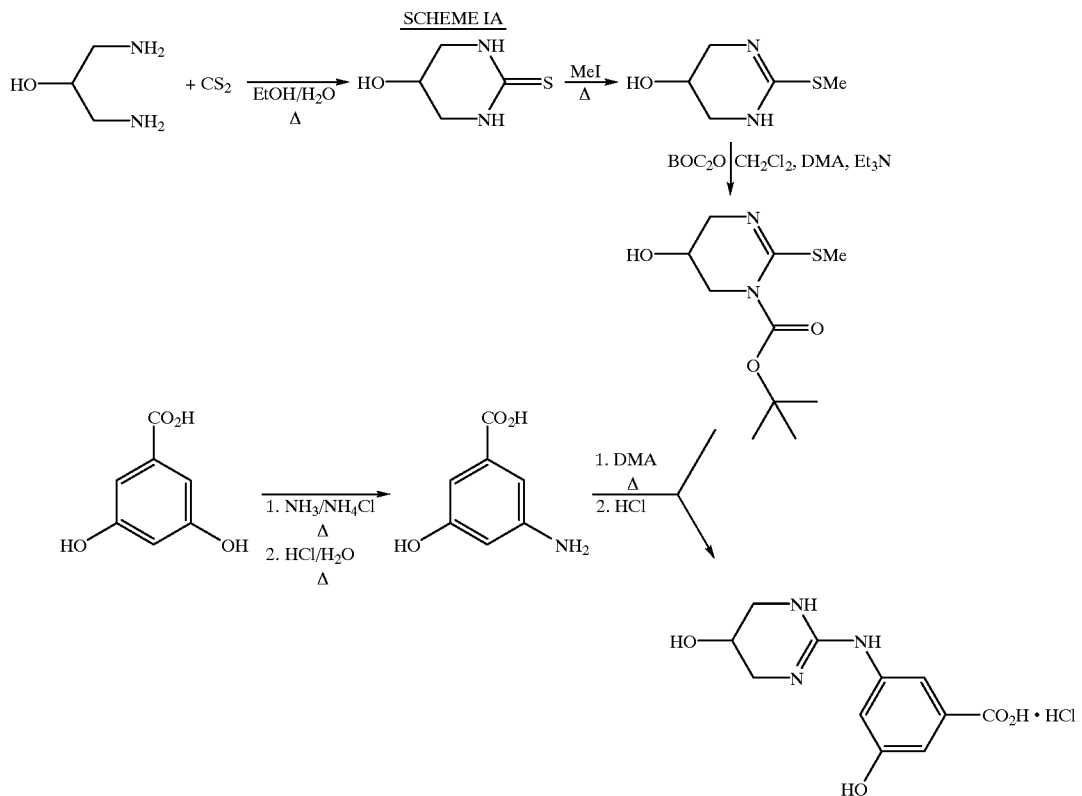

SCHEME IA

Scheme IA illustrates methodology useful for preparing the tetrahydropyrimidinobenzoic acid portion of the $\alpha_v\beta_3$ integrin antagonists described herein which can be coupled to a gly-β-amino acid ester. Briefly, in Scheme IA 1,3-diamino-2-hydroxypropane is reacted with carbon disulfide in an appropriate solvent such as ethanol-water, refluxed, cooled, hydrochloric acid added, refluxed again, cooled and the product, 5-hydroxytetrahydropyrimidine-2-thione harvested by filtration and dried. This cyclic thiourea intermediate is converted to the S-methyl derivative by reaction of thione and methyl iodide in ethanol at reflux. The desired 2-methylthioether-5-hydroxypyrimidine hyciroiodide is readily isolated by removing volatiles at reduced pressure. Thus, 2-methylthioether-5-hydroxypyrimidine hydroiodide in methylene chloride DMA (about 10:1) and an equivalent of triethylamnine are cooled to about ice-bath temperature and an equivalent of di-tert-butyl dicarbonate (BOC anhydride) added. Conventional work-up gives the BOC-2-methylthioether-5-hydroxypyrimidine as an oil.

3,5-dihydroxybenzoic acid is converted to 3-amino-5-hydroxy-benzoic acid using the procedure of *Aust. J. Chem.*, 34 (6), 1319–24 (1981).

The final desired product, 3-hydroxy-5-[(5-hydroxy-1,4,5,6-tetrahydro-2-pyrimidinyl)amino]benzoic acid hydrochloride salt, is prepared by reacting BOC-2-methylthioether-5-hydroxypyrimidine and 3-amino-5-hydroxy-benzoic acid in hot DMA. Upon cooling, a precipitate forms and zwitterionic product isolated by filtration. The HCl salt can be obtained by lyophilizing from dilute hydrochloric acid, for example.

SCHEME II

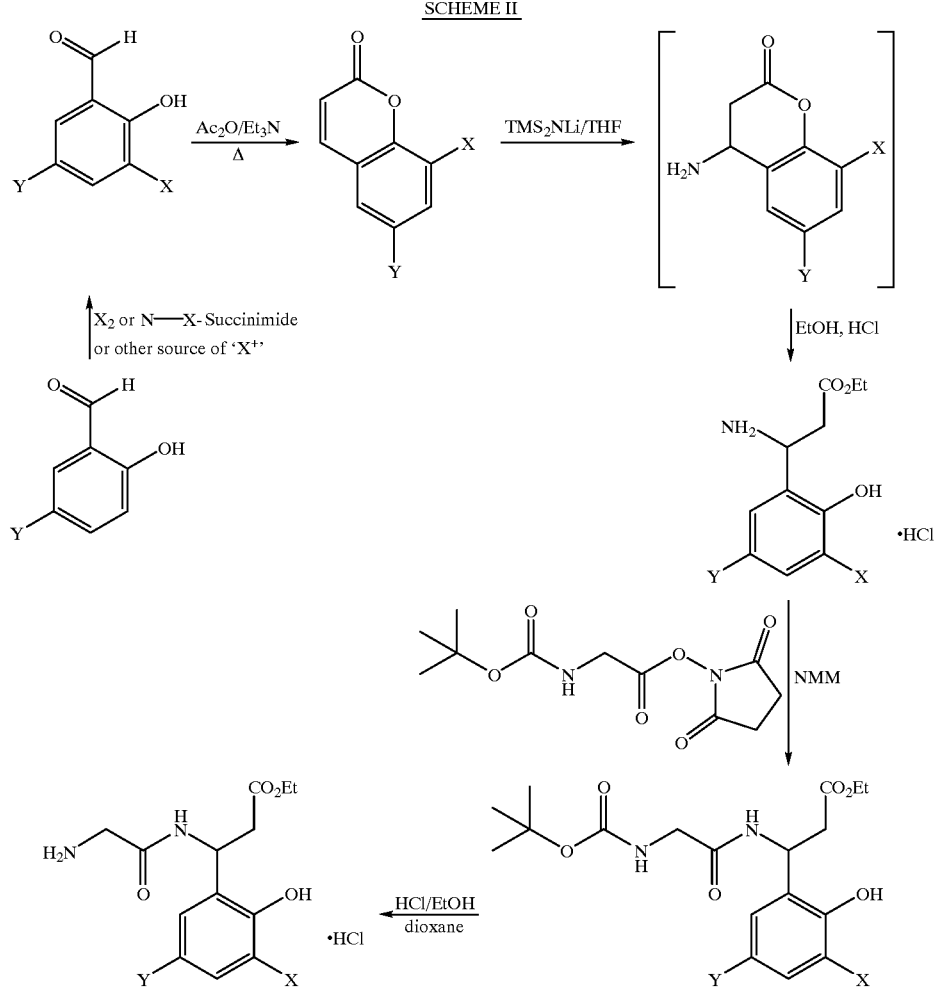

Y and X are halo groups

Scheme II illustrates methodology useful for preparing the ethyl N-gly-amino-3-(3,5-dihalo-2-hydroxy) phenyl propionate which can be coupled to the tetrahydropyrimidinobenzoic acid moiety. Briefly, 3,5-halo substituted salicylaldehydes may be prepared by direct halogenation as, for example, would be the case where 5-bromosalicylaldehyde is slurried in acetic acid and an equivalent or more of chlorine is added to yield 3-chloro-5-bromo-2-hydroxybenzaldehyde. Some product precipitates and can be recovered by filtration. The remainder may be recovered by diluting the filtrate with water and isolating the precipitate. Combining the solids and drying gives 3-chloro-5-bromo-2-hydroxybenzaldehyde. 3-iodo-5-chlorosalicylaldehyde may be prepared by reacting 5-chlorosalicylaldehyde with N-iodosuccinimide in DMF and subjecting the reaction mixture to usual work-up conditions. 3-iodo-5-bromosalicylaldehyde may be prepared by reacting 5-bromosalicylaldehyde in acetonitrile with potassium iodide and chloramine T. Work-up gives a material that when treated with hexanes gives the desired 3-iodo-5-chlorosalicylaldehyde.

Coumarins are readily prepared from salicylaldehydes using a modified Perkin reaction (e.g., *Vogel's Textbook of Practical Organic Chemistry*, 5th Ed., 1989, p. 1040,). The halo-substituted coumarins are converted to 3-aminohydrocoumarins (see J. G. Rico, *Tett. Let.*, 1994, 35, 6599–6602) which are readily opened in acidic alcohol to give 3-amino-3-(3,5-halo-2-hydroxy)phenyl propanoic acid esters.

3-amino-3-(3,5-halo-2-hydroxy)phenyl propanoic acid esters are converted to N-gly-3-amino-3-(3,5-halo-2-hydroxy)phenyl propanoic acid esters by reaction of Boc-N-gly-N-hydroxysuccinimide to give Boc-N-gly-3-amino-3-(3,5-halo-2-hydroxy)phenyl propanoic acid esters that are converted to HX salts of N-gly-3-amino-3-(3,5-halo-2-hydroxy)phenyl propanoic acid esters (wherein X is a halo group) for example, by removal of the BOC-protecting group using HCl in ethanol.

The amino acid compounds used in preparing the $\alpha_v\beta_3$ antagonist compounds can alternatively be prepared according to the chiral synthetic procedures set forth herein and below and according to the methodology described and claimed in co-pending U.S. Ser. No. 60/076,710, filed Mar. 4, 1998.

SCHEME III

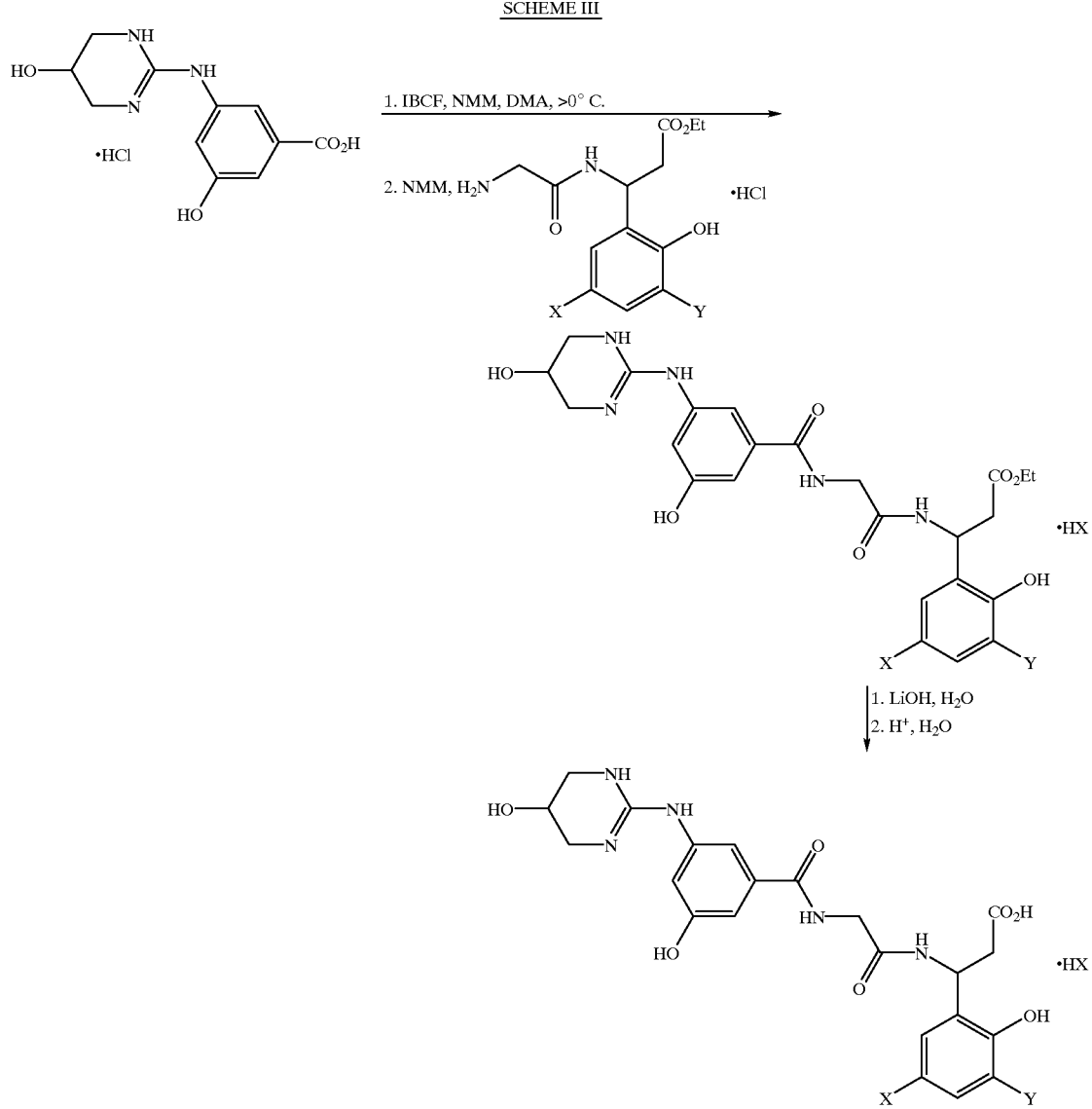

Y and X are halo groups

Scheme III is illustrative of methodology useful for preparing various $\alpha_v\beta_3$ antagonist compounds. 3-Hydroxy-5-[(1,4,5,6-tetrahydro-5-hydroxy-2-pyrimidinyl)amino]benzoic acid is activated to coupling using known methods. Thus, after dissolving in a suitable solvent such as DMA an equivalent of NMM is added. The reaction mixture is cooled to ice-bath temperatures and IBCF added. To the mixed anhydride intermediate is added the gly-β-amino acid ester and NMM. Upon completion of the reaction the product is purified by prep hplc and the ester hydrolyzed to the acid by treating with a base, such as LiOH in a suitable solvent (dioxane/water or acetonitrile/water). Alternatively, a suitable acid, such as TFA can be used. The product is isolated by prep hplc or by isolating the zwitterion at pH 5–7 and converting to the desired salt by standard procedures.

EXAMPLE A

Preparation of

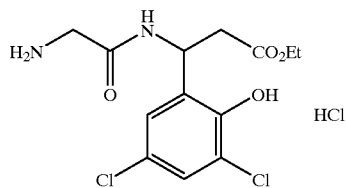
HCl

Step 1

Preparation of

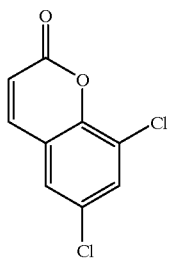

To a 2L round bottom flask fitted with a mechanical stirrer and condenser was added 3, 5-dichlorosalicylaldehycle (200 g, 1.05 mol, 1 equiv.), acetic anhydride (356 g, 3.49 mol) and triethylamine (95.0 g, 0.94 mol, 0.90 equiv.). The reaction solution was heated at reflux overnight. The dark brown reaction mixture was cooled to 50° C. and water (1 L) added with stirring. After one hour the mixture was filtered and the filtrate combined with EtOH (1 L). This mixture was heated to 45° C. for one hour, cooled to room temperature, filtered and the solid (fraction A) washed with EtOH (0.5 L). The combined EtOH solutions were concentrated by rotary evaporation to an oil (fraction B). The solid from fraction A was dissolved in methylene chloride (1.5 L) and the resulting solution passed through a pad of silica gel (1300 mL volume). The resulting dark brown solution was concentrated to an oil that was triturated with hexanes (1.3 L) to give a solid that was isolated by filtration and washed (hexanes) to give substantially pure 6,8-dichlorocoumarin (163 g). A further 31 g of product was obtained by treating the oil, fraction B, in a similar fashion; the oil was dissolved in methylene chloride (0.5 L) passed through a silica pad (0.5 L volume) and triturated with hexanes. The total isolated yield was 194 g or 86% yield of the brown solid.

MS and NMR were consistent with the desired structure.

Step 2

Preparation of

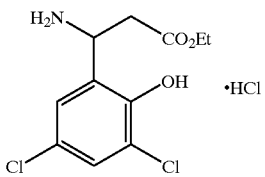
·HCl

To a 3-neck 2L round bottom flask fitted with a mechanical stirrer was added 6,8-dichlorocoumarin (160 g, 0.74 mol) (prepared in Step 1) and dry THF (375 mL, Aldrich Sure Seal). The resulting mixture was cooled to −40° C. (dry ice/acetone bath) and lithium bis(trimethylsilyl)amide (0.80 mol, 800 mL of 1M in THF) added while maintaining temperature below −40° C. After the completion of the addition the cooling bath was removed. After 0.5 hour the mixture had warmed to −5° C. The reaction was quenched by addition of a solution of HCl (0.5 L of 4M in dioxane) in EtOH (1.25 L). The temperature was maintained below 0° C. overnight. The reaction mixture was concentrated to about one-half its original volume and partitioned between EtOAc (3 L) and water (2L). The organic layer was washed with aqueous HCl (3×1L 0.5 N HCl). The pH of the combined aqueous layers was adjusted to about 7 by addition of 10% aqueous NaOH and extracted with methylene chloride (3×2L). The combined organic layers were dried (MgSO$_4$), filtered, and 4M HCl in dioxane (210 mL) added with stirring. Upon completion of precipitation the solid was removed by filtration. The filtrate was concentrated to a small volume and methyl t-butyl ether added. The solid obtained was combined with the initially formed solid and the combined product was washed with methyl t-butyl ether, isolated by filtration and dried (vacuum oven over a weekend) to obtain the desired product (172 g, 740%, yield).

MS and NMR were consistent with the desired structure.

Step 3

Preparation of

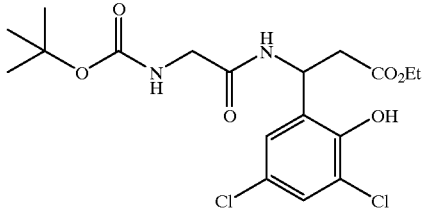

To a flame-dried round bottom flask (0.5 L) equipped with magnetic stir bar was added N-t-Boc-glycine N-hydroxysuccinimide ester (Sigma, 15.0 g, 0.055 mol), dry DMF (Aldrich Sure Seal, 200 mL) and the product from Step 2 (21.67 g, 0.055 mol) under an inert atmosphere (Ar). The reaction mixture was cooled to approximately 0° C. (salt-ice bath) and N-methylmorpholine (5.58 g, 0.056 mole) and a catalytic amount of DMAP added and the reaction allowed to proceed overnight. The reaction mixture was concentrated to a slush, and partitioned between EtOAc (0.4L) and aqueous base (2×0.2 L, aqueous saturated NaHCO$_3$). The organic layer was washed consecutively with aqueous citric acid (2×0.2 L, 10% w/v), again with aqueous sodium bicarbonate (2×0.2 L), brine and dried (Na$_2$SO$_4$). Volatiles were removed under vacuum at 55° C. to give an oil (22.5 g, 92% yield) that solidified on standing.

MS and NMR were consistent with the desired structure.

Step 4

Preparation of

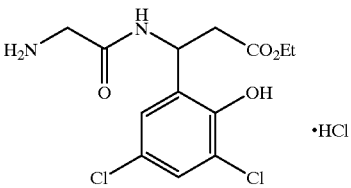
·HCl

The product obtained in Step 3 was de-protected to give the amine hydrochloride salt using the following procedure.

To the product from Step 3 (14.0 g, 0.032 mole) in a flame-dried round bottom flask (0.1 L) with stir bar was added dry dioxane (40 mL). To this was added 4.0 N HCl in dioxane (2 equiv., 6.32 mL) at 0° C. and the reaction allowed to proceed until gas evolution ceased and the reaction was complete. Volatiles were removed under vacuum and the residue triturated with diethyl ether (50 mL). Solids were collected by filtration and washed with ether and dried to give the desired product (12.5 g).

MS and NMR were consistent with the desired structure.

EXAMPLE B

Preparation of

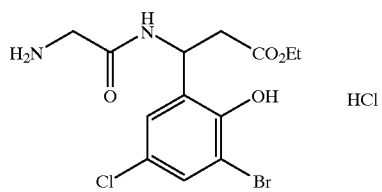

HCl

Step 1

Preparation of

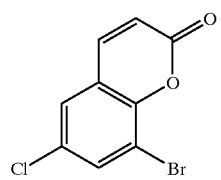

To a suspension of 3-bromo-5-chlorosalicylaldehyde (175.0 g, 743.2 mmol) in acetic anhydride (280.5 mL, 3.0 mol) was added triethylamine (103.6 mL, 743.2 mmol). The reaction solution was heated at reflux for 4.5 hours. The solution was cooled and concentrated in vacuo. To the brown residue was added absolute ethanol (730 mL). The mixture was stored at 0° C. for 14 hours. The brown solid was collected by filtration and washed with cold ethanol. The solid was dried in vacuo to give the desired product (123.0 g, 64% yield). $^1$H NMR was consistent with the proposed structure.

Step 2

Preparation of

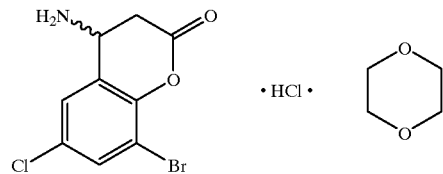

To a suspension of the coumarin (40.0 g, 154.1 mmol) in THF (400 mL) at −76° C. was added, dropwise with stirring, lithium bis(trimethylsilyl)-amide (154.1 mL of a 1M solution in THF). The addition was completed in 10 minutes. The reaction mixture was then stirred for 5 minutes, warmed to −20° C. and stirred for 15 minutes. To this solution was added acetic acid (9.25 g, 154.1 mmol) in THF (28 mL) over 5 minutes. The mixture was warmed to room temperature and volatiles were removed in vacuo. The residue was dissolved in ether (850 mL), washed with saturated aqueous NaHCO$_3$ (2×100 mL), brine (2×40 mL) and dried (MgSO$_4$). The ether solution was concentrated to about 160 mL and cooled to 0° C. To this suspension was added 4M HCl in dioxane (56.3 mL, 225 mmol) and the mixture was stirred at 0° C. for 30 minutes. The suspension was filtered and the filter cake washed with ether. The solid was dried in vacuo to give the desired product as the HCl salt, dioxane solvate, (45.0 g). $^1$H NMR was consistent with the proposed structure.

Step 3

Preparation of

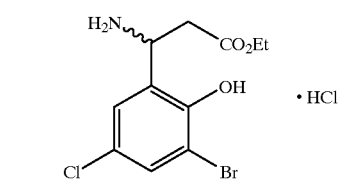

To a suspension of the lactone (142.2 g, 354.5 mmol) in absolute ethanol (533 mL) was added 4M HCl in dioxane (157.8 mL, 631.1 mmol) over 10 minutes. The reaction mixture was stirred at room temperature for 2.5 hours. Volatiles were removed in vacuo. The residue was dissolved in ethyl acetate (450 mL) and the solution kept at 0° C. for 15 hours. The tan precipitate was collected by filtration and washed with cold ethyl acetate. The solid was dried in vacuo to give the desired product as the hydrochloride salt (100.4 g, 79% yield). $^1$H NMR was consistent with the proposed structure.

Step 4

Preparation of

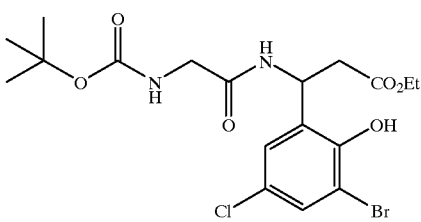

To a flame-dried round bottom flask (0.1 L) equipped with magnetic stir bar was added N-t-Boc-glycine N-hydroxysuccinimide ester (Sigma, 2.72 g, 0.010 mol), dry THF (Aldrich Sure Seal, 50 mL) and the product from Step 3 (3.10 g, 0.01 mole, vacuum desiccated overnight over P$_2$O$_5$) under an inert atmosphere (Ar). The reaction mixture was cooled to approximately 0° C. (salt-ice bath) and triethylamine3 (1.01 g, 0.010 mole) was added. The reaction was allowed to proceed overnight. The reaction mixture was concentrated to a semi-solid and worked up in a fashion similar to Example A, Step 3. Volatiles were removed from the organic layer under vacuum at 55° C. to give an oil (4 g, 83% yield) that solidified on standing.

MS and NMR were consistent with the desired structure.

Step 5
Preparation of

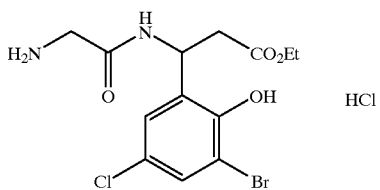

The product obtained in Step 4 was de-protected to give the amine hydrochloride salt using the following procedure. To the product from Step 4 (4.0 g, 0.0084 mole) in a flame-dried round bottom flask (0.1 L) with stir bar was added dry dioxane (20 mL). To this was added 4.0 N HCl in dioxane (20 mL) and the reaction allowed to proceed until gas evolution ceased and the reaction was complete (about one hour). Volatiles were removed under vacuum and the residue triturated with diethyl ether (50 mL). Solids were collected by filtration and washed with ether and dried to give a light brown solid (2.7 g, 78% yield).

MS and NMR were consistent with the desired structure.

EXAMPLE C
Preparation of

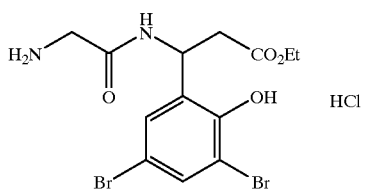

Step 1

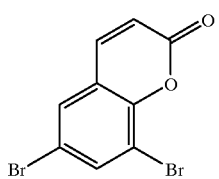

To a suspension of 3,5-dibromosalicylaldehyde (100 g, 357 mmol) in acetic anhydride (164.8 mL, 1.8 mol) was added triethylamine (45 mL, 375 mmol). The reaction solution was heated overnight at reflux under argon. The solution was cooled to room temperature and a solid mass formed. The dark brown reaction mixture was washed with hot hexanes (3×300 mL) and aqueous saturated sodium bicarbonate. The resulting solid was dissolved in EtOAc (2L) and washed with water. The organic layer was dried (sodium sulfate) and concentrated to give a brown solid that was collected by filtration. The solid was dried in vacuo to give substantially pure 6,8-dibromocoumarin (94.2 g, 87% yield).

MS and $^1$H NMR were consistent with the desired structure.

Step 2

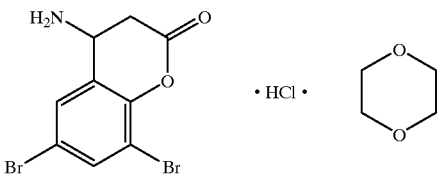

To 6,8-dibromocoumarin (20.0 g, 0.066 mol) (prepared in Step 1) in THF (100 mL) at −78° C. was added dropwise with stirring lithium bis(trimethylsilyl)amide (66 mL of a 1M solution in THF). The addition was completed in 10 minutes. The reaction mixture was then stirred for 5 minutes, warmed to 0° C. and stirred for 15 minutes. To this solution was added acetic acid (3.95 g) over one minute. The mixture was warmed to room temperature and volatiles were removed in vacuo. The residue was dissolved in hexanes (500 mL), washed with saturated aqueous NaHCO$_3$ (2×100 mL) and dried (Na$_2$SO$_4$). The organic solution was concentrated to give an oil that was immediately taken up in diethyl ether (400 mL) and 4M HCl in dioxane (30 mL) was added with stirring at 0° C. for 30 minutes. Excess HCl was removed in vacuo, the suspension filtered and the filter cake washed with ether. The solid was dried in vacuo to give the desired product as the HCl salt, dioxane solvate (19.9 g).

MS and $^1$H NMR were consistent with the desired structure.

Step 3

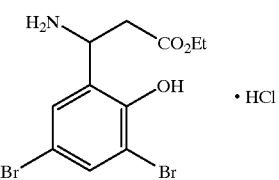

The lactone prepared in Step 2 above (15 g) was dissolved in absolute ethanol (400 mL) and anhydrous HCl gas was passed through for one minute. The reaction mixture was stirred at room temperature for 2.5 hours. RPHPLC showed complete reaction. The volatiles were removed in vacuo to give a dark residue. The residue was triturated with diethyl ether (500 mL) and the mixture stirred overnight. The tan precipitate was collected by filtration and washed with diethyl ether. The solid was dried in vacuo to give the desired product as the hydrochloride salt (15.2 g).

MS and $^1$H NMR were consistent with the desired structure.

Step 4

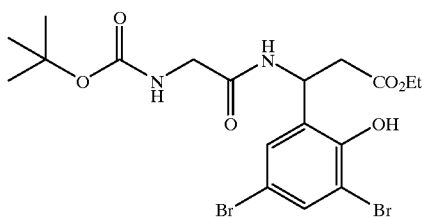

To a flame-dried round bottom flask (0.2 L) equipped with magnetic stir bar was added N-t-Boc-glycine N-hydroxysuccinimide ester (Sigma, 8.1 g, 0.030 mol), dry DMF (Aldrich Sure Seal, 50 mL) and the product of Step 3 (12 g, 0.03 mole, vacuum desiccated overnight over $P_2O_5$) under an inert atmosphere (Ar). The reaction mixture was cooled to approximately 0° C. (salt-ice bath) and N-methyl morpholine (3.03 g, 0.030 mole) and catalytic DMAP added. The reaction was allowed to proceed overnight warming to room temperature. The reaction mixture was concentrated to a semi-solid and worked up in a fashion similar to Example A, Step 3. Volatiles were removed from the organic layer under vacuum at 55° C. to give an oil (15.7 g, 93% yield) that solidified on standing.

MS and NMR were consistent with the desired structure.

Step 5

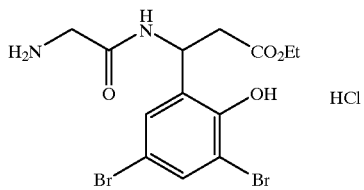

The product obtained in Step 4 was deprotected to give the amine hydrochloride salt using the following procedure. To the product from Step 4 (13.0 g, 0.0084 mole) in a flame-dried round bottom flask (0.1 L) with stir bar was added dry dioxane (40 mL). To this was added 4.0 N HCl in dioxane (30 mL) and the reaction allowed to proceed until gas evolution ceased and the reaction was complete (about one hour). The volatiles were removed under vacuum and the residue triturated with diethyl ether (50 mL). Solids were collected by filtration and washed with ether and dried to give a solid (10.6 g, 93% yield).

MS and NMR were consistent with the desired structure.

EXAMPLE D

Preparation of

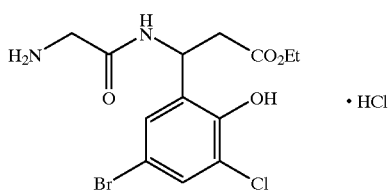

Step 1
Preparation of 3-chloro-5-bromosalicylaldehyde

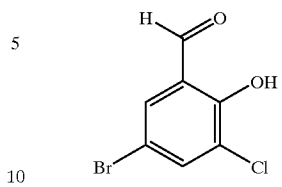

To a 5L round bottom flask fitted with a mechanical stirrer and gas addition tube was added 5-bromosalicylaldehyde (495 g, 2.46 mol) and acetic acid at ambient temperature to form a slurry. To this mixture was added chlorine gas at a moderate rate until a slight molar excess of chlorine (183 g, 1.05 mol) had dissolved. After the addition was stopped the reaction allowed to proceed overnight. The solid formed was recovered by filtration and the filtrate diluted into water (2.5L). The mixture was stirred vigorously for 20 minutes, the product collected by filtration and washed with water. The combined solids were vacuum dried to give the desired 3-chloro-5-bromosalicylaldehyde (475 g, 82% yield).

MS and $^1$H NMR were consistent with the desired structure.

Step 2
Preparation of 6-bromo-8-chlorocoumarin

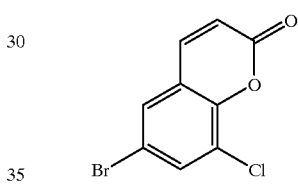

To a 5L round bottom flask fitted with a mechanical stirrer and condenser was placed 3-chloro-5-bromosalicylaldehyde (554.1 g, 2.35 mol, 1 equiv.), acetic anhydride (1203 g, 11.8 mol, 5 equiv.) and triethylamine (237.4 g, 2.35 mol, 1 equiv.). The reaction solution was heated at reflux (131–141° C.) overnight. The dark brown reaction mixture was cooled to 50° C. and ice (2 L) added (ice-bath cooling) with stirring. After one hour the mixture was filtered and the filtrate combined with EtOH (1 L). To this mixture was added EtOH (300 mL) and the reaction mixture stirred for one hour. The precipitate that formed was collected by filtration and washed with water: EtOH (3×1.3 L), vacuum and dried then dried on a fluid-bed drier. The total isolated yield is 563 g or 92%.

MS and $^1$H NMR were consistent with the desired structure.

Step 3
Preparation of 3-amino-3-(2-hydroxy-3-chloro-5-bromo) phenyl propanoic acid ethyl ester

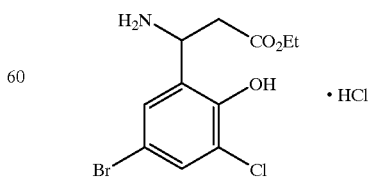

To a 3-neck 5L round bottom flask fitted with a mechanical stirrer was added 6-bromo-8-chlorocoumarin (300 g, 1.16 mol) (prepared in Step 2) and dry THF (900 mL, Aldrich Sure Seal). The resulting mixture was cooled to less than −45° C. (dry ice/acetone bath) and lithium bis(trimethylsilyl)amide (0.80 mol, 800 mL of 1M in THF and 0.6 L in hexanes, 1.2 equivalents) added while maintaining temperature below −45° C. for 0.5 hour. In a separate 5L flask EtOH (2.5 L) and HCl (4 N HCl in dioxane, 1 L) were combined at −15° C. The coumarin reaction was quenched by addition of the cooled HCl/EtOH solution. After 0.5 hour the resulting reaction mixture temperature was −8.3° C. The reaction mixture was kept at 0° C. overnight, concentrated to about 2.5 L and partitioned between EtOAc (3 L) and water (4 L). The organic layer was washed with aqueous HCl (4×1.2 L, 0.5 N HCl). The pH of the combined aqueous layers was adjusted to about 8 by addition of 10% aqueous NaOH and extracted with methylene chloride (1×7 L and 3×2L). The combined organic layers were dried (MgSO$_4$, 900 g), filtered, and 4M HCl in dioxane (400 mL) added with stirring. Upon completion of precipitation the solid was removed by filtration. The mixture was concentrated to 2.5 L, hexanes added (2.5 L) and the precipitate isolated by filtration. The filter cake was washed with methylene chloride/hexanes (1:2), suction dried and vacuum oven dried at 40° C. to obtain the desired product (251 g, 60% yield).

MS and $^1$H NMR were consistent with the desired structure.

Step 5

Preparation of

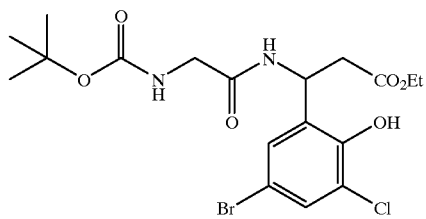

The above compound was prepared using essentially the same procedure and relative quantities as specified for its isomer in Example B, Step 4.

MS and $^1$H NMR were consistent with the desired structure.

Step 6

Preparation of

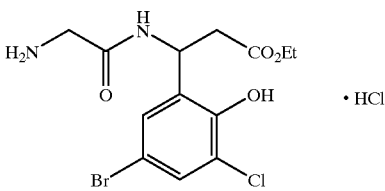

This compound was prepared using essentially the same procedure and relative quantities as specified for its isomer in Example B, Step 5.

MS and $^1$H NMR were consistent with the desired structure.

EXAMPLE E

Preparation of

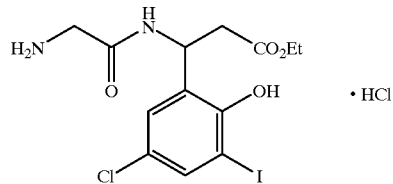

Step 1

Preparation of 3-iodo-5-chlorosalicylaldehyde.

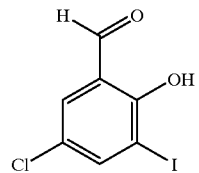

N-Iodosuccinimide (144.0 g, 0.641 mole) was added to a solution of 5-chlorosalicylaldehyde (100 g, 0.638 mole) in dimethylformamide (400 mL). The reaction mixture was stirred for 2 days at room temperature. Additional N-iodosuccinimide (20.0 g) was added and the stirring was continued for an additional 2 days. The reaction mixture was diluted with ethyl acetate (1 L), washed with hydrochloric acid (300 mL, 0.1 N), water (300 mL), sodium thiosulfate (5%, 300 mL), brine (300 mL), dried (MgSO$_4$) and was concentrated to dryness to afford the desired aldehyde (162 g, 90% yield) as a pale yellow solid.

MS and NMR were consistent with the desired structure.

Step 2

Preparation of 6-chloro-8-iodocoumarin

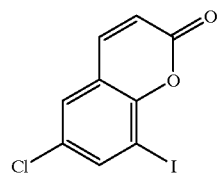

A mixture of 3-iodo-5-chlorosalicylaldehyde (100 g, 0.354 mole), acetic anhydride (300 mL) and triethylamine (54 mL) was heated at reflux for 18 hours. Upon cooling, the desired coumarin precipitated as a dark brown crystalline material. This was filtered, washed with hexane/ethyl acetate (4:1, 200 mL), and was air dried. Yield: 60 g (55%).

MS and $^1$H NMR were consistent with the desired structure.

Step 3

Preparation of (R,S)-4-amino-3,4-dihydro-6-chloro-8-iodocoumarin hydrochloride.

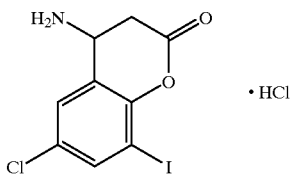

Lithium hexamethyidisilazane (21.62 mL, 1M, 21.62 mmol) was added to a solution of 6-chloro-8-iodocoumarin (6.63 g, 21.62 mmol) in tetrahydrofuran (100 mL) at −78° C. The reaction mixture was stirred at this temperature for 30 minutes, then at 0° C. for 1 hour. Acetic acid (1.3 g, 21.62 mmol) was added to the reaction mixture. The reaction mixture was poured into ethyl acetate (300 mL) and saturated sodium carbonate (200 mL) solution. The organic layer was separated, washed with brine (200 mL), dried (MgSO$_4$), and was concentrated to afford a residue. The residue was added to anhydrous ether (200 mL) followed by dioxane/HCl (4N, 30 mL) at 0° C. The reaction mixture was stirred for 1 hour at room temperature, filtered, and was dried in vacuo to afford the desired product (4.6 g, 59% yield) as a powder. (RPHPLC: Rf 6.8 minutes; Gradient 10% acetonitrile −90% acetonitrile over 15 minutes then to 100% acetonitrile over the next 6 minutes. Both water and acetonitrile contain 0.1% TFA. Vydac C18 protein peptide column, 2 mL/minutes flow rate, monitored at 254 nm).

MS and $^1$H NMR were consistent with the desired structure.

Step 4

Preparation of (R,S)-Ethyl 3-amino-3-(5-chloro-2-hydroxy-3-iodo)phenyl propionate hydrochloride.

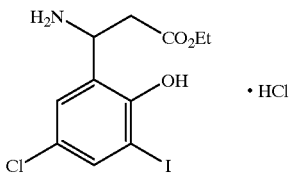

Hydrogen chloride gas was bubbled into a solution of 4-amino-3,4-dihydro6-chloro-8-iodocoumarin hydrochloride (22.0 g, 61.09 mmol) in ethanol (250 mL) keeping the reaction mixture at 0–10° C. till saturation. After 6 hours at reflux, most of the solvent was removed by distillation. The cooled residue was added to anhydrous ether and was stirred for 2 hours. The initial gum turned into a crystalline material. The crystalline product was filtered and was dried to afford the desired product (20 g, 81% yield) as a off-white crystalline powder. (Rf 7.52 minutes, conditions as Step 3).

MS and $^1$H NMR were consistent with the desired structure.

Step 5

Preparation of (R,S)-ethyl 3-(N-BOC-gly)-amino-3-(5-chloro-2-hydroxy-3-iodo phenyl propionate.

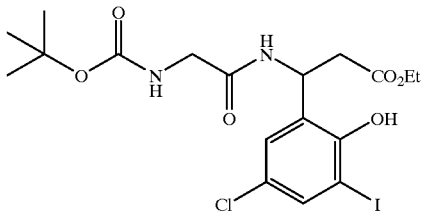

A mixture of BOC-gly (2.16 g, 12.31 mmol), HOBT (1.67 g, 12.31 yield), EDCl (2.36 g, 12.31 mmol) and DMF (50 mL) was stirred at 0° C. for 1 hour. Ethyl 3-amino-3-(5-chloro-2-hydroxy-3-iodo)propionate hydrochloride (5.0 g, 12.31 mmol) was added to the reaction mixture followed by triethylamine (3.5 mL). The reaction mixture was stirred for 18 hours at room temperature. DMF was removed irg vacuo and the residue was partitioned between ethyl acetate (300 mL) and sodium bicarbonate (200 mL). The organic layer was washed with hydrochloric acid (1N, 100 mL), brine (200 mL), dried (MgSO$_4$) and was concentrated to afford the desired product as a solid (6 g, 93% yield).

MS and $^1$H NMR were consistent with the desired structure.

Step 6

Preparation of (R,S)-ethyl 3-(N-gly)-amino-3-(5-chloro-2-hydroxy-3-iodo)phenyl propionate hydrochloride.

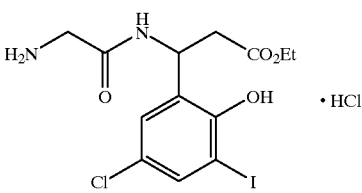

Dioxane/HCl (4N, 20 mL) was added to ethyl 3-(N-BOC-gly)-amino-3-(5-chloro-2-hydroxy-3-iodo)propionate (6.0 g, 11.39 mmol) at 0° C. and was stirred at room temperature for 3 hours. The reaction mixture was concentrated, and concentrated once more after addition of toluene (100 mL). The residue obtained was suspended in ether and was filtered and dried to afford the desired product as a crystalline powder (5.0 g, 95% yield). (RPHPLC: Rf 8.3 minutes, conditions as in Step 3).

MS and $^1$H NMR were consistent with the desired structure.

EXAMPLE F

Preparation of

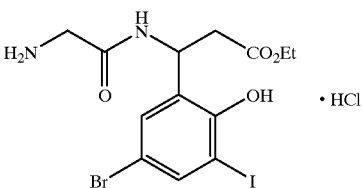

Step 1

Preparation of 3-iodo-5-bromosalicylaldehyde

To a solution of 5-bromosalicylaldehyde (20.0 g, 0.1 mole) and potassium iodide (17 g, 0.1 mole) in acetonitrile (150 mL) and water (50 mL) in a 500 mL round bottom flask with magnetic stirrer was added chloramine T (23 g, 0.1 mole). The mixture was allowed to react for one hour. The reaction mixture was partitioned between hydrochloric acid (10%, 200 mL) and ethyl acetate. The organic layer was dried (Na$_2$SO$_4$), filtered and concentrated in vacuo. To the residue was added hexanes and the reaction mixture heated to 50° C. for 15 minutes. The undissolved material was removed by filtration. The filtrate was concentrated in vacuo to leave canary yellow 3-iodo-5-bromosalicylaldehyde (26 g).

MS and $^1$H NMR were consistent with the desired structure.

Step 2

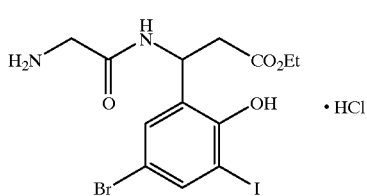

The above compound was prepared using essentially the same procedure of Example E, Steps 2–6 where in Step 2, an equivalent amount of product from Step 1, 3-iodo-5-bromo-salicylaldehyde, was substituted for 3-iodo-5-chlorosalicylaldehyde.

MS and $^1$H NMR were consistent with the desired structure.

EXAMPLE H

Preparation of

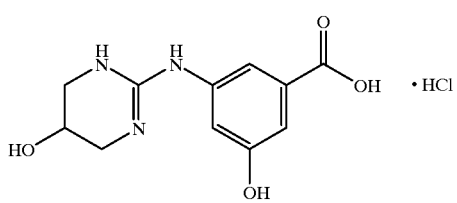

Step 1

Ethanol (375 mL) and deionized water (375 mL) were added to a 2L 3-neck round bottom flask fitted with a mechanical stirrer, Claisen adapter, addition funnel, reflux condenser and thermocouple. 1,3-diamino-2-hydroxypropane (125.04 g, 1.39 mol) (Aldrich) was added to the reaction flask and stirred to dissolve. Carbon disulfide (84 mL, 1.39 mol) was added in a drop-wise fashion via addition funnel at 25–330° C. over a 35 minute period to afford a milky-white mixture. The temperature was maintained with an ice bath. The reaction mixture was refluxed at 73.4° C. for two hours to afford a yellow solution. The reaction mixture was cooled with an ice bath to 25° C. and concentrated HCl (84 mL) was added in dropwise fashion while maintaining the temperature at 25–26° C. The reaction mixture was refluxed for 21 hours at 78.4° C. The reaction solution was cooled to 2° C. and product collected via vacuum filtration. The white solid was washed 3 times with ice bath chilled ethanol: water (1:1) (50 mL) and dried in vacuo at 40° C. to afford 5-hydroxytetrahydropyrimidine-2-thione (63.75 g, 34.7% yield) as a white solid.

MS and NMR were consistent with the desired structure.

Step 2

5-Hydroxytetrahydropyrimidine-2-thione (95 g, 0.72 mol) prepared in Step 1, absolute ethanol (570 mL), and methyl iodide (45 mL, 0.72 mol) were added to a 2 L round bottom flask fitted with a mechanical strirrer and thermocouple. The reaction mixture was refluxed at 78° C. for 5 hours and then cooled to room temperature. The reaction mixture was concentrated in vacuo to afford a white solid (194.72 g). The while solid was triturated 3 times with ethyl ether (500 mL ) and dried in vacuo to afford 2-methylthioether-5-hydroxypryrimidine hydroiodide (188.22 g, 95.4% yield) as a white solid.

MS and $^1$H NMR were consistent with the desired structure.

Step 3

2-Methyl thioether-5-hydroxypyrimidine hydroiodide (150.81 g, 0.55 mol), methylene chloride (530 mL), dimethylacetamide (53 mL) and triethylamine (76.7 mL, 0.55 mol) were added to a 2L 3-neck round bottom flask fitted with reflux condenser, mechanical stirrer and a static atmosphere of nitrogen. The mixture was cooled with an ice bath and di-tert-butyl dicarbonate (120.12 g, 0.55 mol) was added at 4° C. The reaction mixture was heated at 42.5° C. for 18 hours to afford a light yellow solution. The reaction solution was transferred to a 2L separatory funnel and washed 3 times with DI water (200 mL), dried with MgSO$_4$, filtered and concentrated in vacuo to afford Boc-2-methylthioether-5-hydroxypyrimidine (134.6 g, 99.35% yield) as a light yellow viscous oil.

MS and $^1$H NMR were consistent with the desired structure.

Step 4

Boc-2-methylthioether-5-hydroxypyrimidine (50.3 g, 0.204 mol), 3-amino-5-hydroxybenzoic acid (Aust. J. Chem. (1981) 34(6), 1319–24) (25.0 g, 0.1625 mole) and 50 mL anhydrous DMA were heated at 100° C. with stirring for 2 days. A slurry precipitate resulted. The reaction was cooled to room temperature and the precipitate was filtered, washed with CH$_3$CN, then ethyl ether and dried. This solid was slurried in H$_2$O and acidified with concentrated HCl resulting in a solution. This was frozen and lyophilized to yield the desired product as a white solid (14.4 g).

MS and $^1$H NMR were consistent with the desired structure.

EXAMPLE I

Preparation of

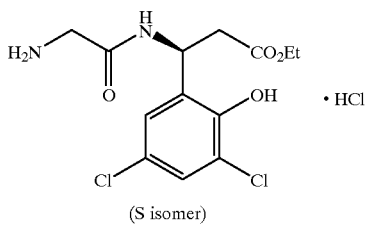

(S isomer)

Step 1
Preparation of Reformatsky Reagent

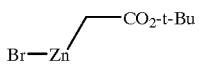

A 4-L flask fitted with a condenser, temperature probe and mechanical stirrer was charged with Zn metal (180.0 g, 2.76 mol, −30–100 mesh) and THF (1.25 L). While stirring, 1,2-dibromoethane (4.74 mL, 0.05 mol) was added via syringe [alternatively, TMS Cl (0.1 equivalent) at room temperature for one hour can be substituted]. After inert gas purge (3 $N_2$/vacuum cycles) the suspension of zinc in THF was heated to reflux (65° C.) and maintained at this temperature for 1 hour. The mixture was cooled to 50° C. before charging tert-butyl bromoacetate (488 g, 369 mL, 2.5 mol) via 50 mL syringe and syringe pump (delivery set to 4.1 mL/minutes) over 1.5 hours. Reaction temperature of 50°+/−5° C. was maintained throughout the addition. The reaction mixture was allowed to stir at 50° C. for one hour after the addition was complete. Subsequently, the mixture was allowed to cool to 25° C. and the precipitated product allowed to settle. The THF mother liquor was decanted into a 2-L round bottom flask using a coarse fritted filter stick and partial vacuum transfer (20 mm Hg). This removed about 65% of the THF from the mixture. 1-Methyl-2-pyrrolidinone (NMP, 800 mL) was added and agitation resumed for 5 minutes. The reaction mixture can be filtered to remove any remaining zinc. Analysis indicated a titer of desired Reformatsky reagent of 1.57 M with a molar yield of 94%. Alternatively, the solid reagent can be isolated by filtration from the original reaction mixture. The cake can be washed with THF until a white solid is obtained and dried under $N_2$ to obtain the desired product as a mono THF solvate that may be stored at −20° C. (desiccated) for extended periods. Typical recoveries are 85–90%.

Step 2
2A. Preparation of

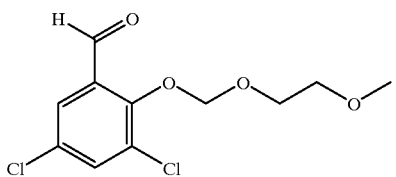

Potassium carbonate (powder, oven dried at 100° C. under vacuum, 8.82 g, 60 mmoles) was added to a solution of 3,5-dichlorosalicylaldehyde (11.46 g, 60 moles) in DMF (40 mL) at room temperature to give a bright yellow slurry. MEMCl (neat, 7.64 g, 61 mmoles) was then added while maintaining the bath temperature at 20° C. The mixture was then stirred at 22° C. for 6 hours and MEMCl (0.3 g, 2.4 mmoles) was added. The mixture was stirred for another 0.5 hour and the reaction mixture poured into cold water (200 mL) to precipitate the product. The slurry was filtered on a pressure filter and the cake was washed with water (2×50 mL) and was dried under $N_2$/vacuum to afford the product (14.94 g, 89%) as a off white solid. $^1$H NMR ($CDCl_3$, TMS) 3.37 (s, 3H), 3.54 to 3.56 (m, 2H), 3.91 to 3.93 (m, 2H), 5.30 (s, 2H), 7.63 (d, 1H), 7.73 (d, 1H), 10.30 (s, 1H); $^{13}$C NMR ($CDCl_3$, TMS) d (ppm):59.03, 70.11, 99.57, 126.60, 129.57, 130.81, 132.07, 135.36, 154.66, 188.30. DSC: 48.24° C. (endo 90.51 J/g); Microanalytical: calcd for $C_{11}H_{12}Cl_2O_4$: C: 47.33%; H: 4.33%; Cl: 25.40%; found: C: 47.15%; H:4.26%; Cl: 25.16%.

2B. Preparation of

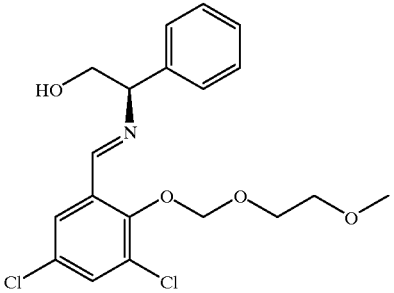

The product from Step 2A (35.0 g, 0.125 mol) was charged in a 1-L 3-neck round bottom flask fitted with a mechanical stirrer and an addition funnel followed by addition of THF (200 mL).The solution was stirred at 22° C. and (S)-phenylglycinol (17.20 g, 0.125 mol) was then added at once. After 30 minutes at 22° C., $MgSO_4$ (20 g) was added. The mixture was stirred for 1 hour at 22° C., and filtered on a coarse fritted filter. The filtrate was concentrated under reduced pressure. No further purification was performed and the crude imine was used directly in the coupling reaction, Step 2C.

Preparation of

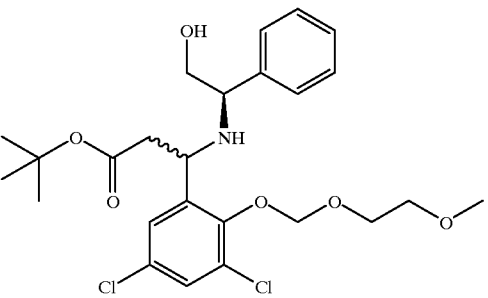

A 1-L 3-neck round bottom flask fitted with a mechanical stirrer and an addition funnel was charged with the solid reagent produced in Step 1 (91.3 g, 0.275 mol) and NMP (200 mL) under nitrogen. The solution was then cooled to −10° C. and stirred at 350 rpm. A solution of imine (prepared in Step 2B) in NMP was prepared under nitrogen and then added over 20 minutes to the above reaction mixture while the temperature was maintained at −5° C. (jacket temperature −10° C.). The mixture was stirred for an additional 1.5 hours at −8° C. and one hour at −5° C. after the addition was complete. After cooling to −10° C. a mixture of concentrated HCl/saturated solution of $NH_4Cl$ (8.1 mL/200 mL) was added in 10 minutes. MTBE (200 ml) was added and the mixture was stirred 15 minutes at 23° C. at 200 rpm. Stirring was stopped and the layers separated. The aqueous layer was extracted with MTBE (100 mL). The two organic layers were combined, washed successively with a saturated solution of $NH_4Cl$ (100 mL), water (100 mL) and brine (100 mL). The solution was dried with $MgSO_4$ (30 g), filtered and concentrated to afford an orange oil (66.3 g) (solidifies in standing) containing the desired product as a single diastereoisomer (confirmed by proton and carbon nmr). A sample was purified for analysis by recrystallization from heptane to afford the product as an off-white solid.

Proton and carbon NMR and IR spectra were consistent with the desired structure. $[\alpha]^P_{25}=+8.7°$ (c=1.057, MeOH). Microanalytical: calcd for $C_{25}H_{33}Cl_2NO_6$: C: 58.77%; H: 6.47%; N: 2.72%; Cl: 13.78%; found: C: 58.22%; H: 6.54%; N: 2.70%; Cl:13.66%.

Step 3

Preparation of

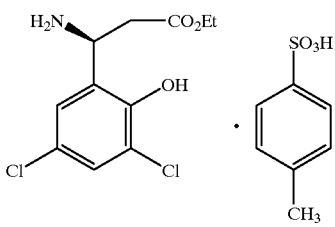

3A. A solution of the crude ester prepared in Step 2 [17.40 g, 0.033 mole (theory)], and EtOH (250 mL) was charged to a 1-L 3-neck jacketed reactor. The solution was cooled to 0° C. and Pb $(OAc)_4$ (14.63 g, 0.033 mole) was added at once. After 2 hours a 15% solution of NaOH (30 mL) was added and ethanol was removed under reduced pressure. Another portion of 15% NaOH (100 mL) was added and the mixture extracted with MTBE (2×100 mL), washed with $H_2O$ (2×100 mL) and brine (50 mL), dried with $Na_2SO_4$, filtered on celite and concentrated under reduced pressure to afford an orange oil (12.46 g). The oil was homogeneous by thin layer chromatography (tlc) and was used without further purification.

3B. The oil from 3A was diluted with EtOH (30 mL) and paratoluene sulfonic acid (1.3 equiv., 0.043 mole, 8.18 g) was added. The solution was heated to reflux for 8 hours, cooled to ambient temperature and concentrated under reduced pressure. The residue was treated with THF (20 mL) and heated to reflux to form a solution. The solution was cooled to room temperature and the compound crystallized. Heptane (30 mL) and THF (10 mL) were added to form a fluid slurry which was filtered. The cake was washed with THF/heptane (40 mL, 1/1) and vacuum dried for two hours in a pressure filter under nitrogen to afford a white solid (7.40 g).

Proton and carbon NMR and IR spectra were consistent with the desired product as substantially a single enantiomer.

Microanalytical: calcd for $C_{18}H_{21}Cl_2NO_6S$, 0.25 $C_4H_8O$: C: 48.73%; H: 4.95%; N: 2.99%; Cl: 15.14%; found: C: 48.91%; H: 4.95%; N: 2.90%; Cl:14.95%.

Step 4

Preparation of

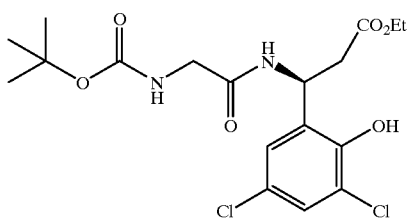

To a 500 mL round bottom flask equipped with a magnetic stir bar and nitrogen bubbler were charged the free base of the product produced in Step 3 (21.7 g, 0.065 mole), N-t-Boc-glycine N-hydroxysuccinimide ester (17.7 g, 0.065 mole) and DMF (200 mL). The reaction mixture was stirred under nitrogen at room temperature for 3.25 hours and a pale orange solution formed. The reaction mixture was poured into ice-cold ethyl acetate (1.2 L). The organic solution was washed with 1 M HCl (250 mL) and then with brine (500 mL), dried ($MgSO_4$) and concentrated under vacuum to near dryness to obtain an oil that was subsequently dried at 50° C. to obtain the product as a colorless oil (28.12 g, 99%). Seed crystals were prepared from ethyl acetate/hexanes. The product (about 28 g) was dissolved in ethyl acetate (35 mL) and hexanes (125 mL). The solution was seeded with the seed crystals and precipitate formed. The solids were filtered and dried overnight under vacuum at 55° C. to yield a colorless solid (27.0 g, 95%).

MS and $^1H$ NMR were consistent with the desired structure.

Step 5

Preparation of

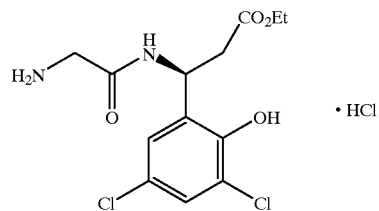

The Boc-protected glycine amide prepared in Step 4 (27.0 g, 0.062 mole) was dried overnight over $P_2O_5$ and NaOH pellets. The solid was dissolved in dioxane (40 mL) and the solution cooled to 0° C. An equivalent volume of 4N HCl/dioxane (0.062 mole) was added and the reaction was run for 2 hours. At this point the conversion was 80% by RPHPLC. The reaction mixture was allowed to warm to room temperature over 4 hours. The reaction mixture was concentrated at 40° C. to a foam which was triturated with ether (200 mL). The white solid that formed was filtered and dried over $P_2O_5$ to yield the desired glycine beta-amino acid ethyl ester compound, as an HCl salt (20.4 g, 88.5% isolated yield).

MS and $^1H$ NMR were consistent with the desired structure.

EXAMPLE J

Preparation of

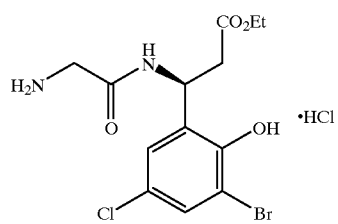

Step 1
Preparation of

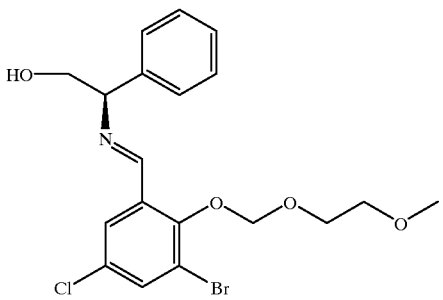

MEM protected 3-bromo-5-chlorosalicylaldehyde (129.42 g, 0.4 mol), prepared according to the procedure of Example I, Step 2A. An equivalent amount of 3-bromo-5-chlorosalicylaldehyde was substituted for 3,5-dichlorosalicylaldehyde, which was charged in a 2-L 3-neck round bottom flask fitted with a mechanical stirrer, followed by addition of THF (640 ml) and (S)-phenylglycinol (54.86 g, 0.4 mol). After 30 minutes at 22° C., MgSO$_4$ (80 g) was added. The mixture was stirred for 2 hours at 22° C., and filtered on a coarse fritted filter. The filtrate was concentrated under reduced pressure to afford a pale yellow oil (180.0 g) containing the desired imine. No further purification was performed and the crude product was used directly in the coupling reaction, Step 2.

Microanalytical: calcd for $C_{19}H_{21}BrClNO_4$: C: 51.54%; H: 4.78%; N: 3.16%; Br: 18.04%; Cl: 8.00%; found: C: 50.22%; H: 4.94%; N: 2.93%; Br: 17.15%; Cl:7.56%.

Step 2
Preparation of

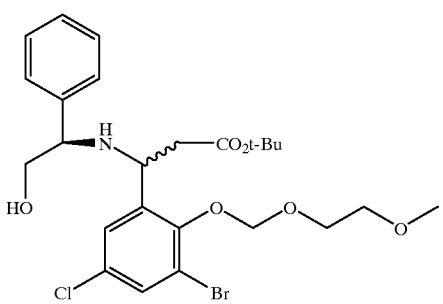

In a 5-L 3-neck round bottom flask fitted with a mechanical stirrer, the reagent from Example I, Step 1 (332.0 g, 0.8 mol) was taken up in NMP (660 mL) under nitrogen. The solution was then cooled to −10° C. A solution of imine from Step 1 in NMP (320 ml) was prepared under nitrogen and then added over 30 minutes to the above reaction mixture while the temperature was maintained at −5° C. The mixture was stirred for an additional hour at −8° C. and at −5° C. for 2 hours after addition was complete and then cooled to −10° C. A mixture of concentrated HCl/saturated solution of NH$_4$Cl (30 mL/720 mL) was added over 10 minutes. MTBE (760 ml) was added and the mixture was stirred for 30 minutes at 23° C. Stirring was stopped and the layers separated. The aqueous layer was extracted with MTBE (320 ml). The organic layers were combined, washed successively with saturated aqueous NH$_4$Cl (320 ml), DI water (320 ml) and brine (320 ml). The solution was dried with MgSO$_4$ (60 g), filtered and concentrated to afford a yellow oil (221.0 g) containing the desired product as a single diastereoisomer as determined by proton NMR. DSC: 211.80° C. (endo. 72.56 J/g), 228.34° C. (98.23 J/g); Microanalytical: calcd for $C_{25}H_{33}BrClNO_6$: C: 53.72%; H: 5.95%; N: 2.50%; Br: 14.29%; Cl: 6.33%; found: C: 52.11%; H: 6.09%; N: 2.34%; Br: 12.84%; Cl:6.33%.

Step 3

Preparation of

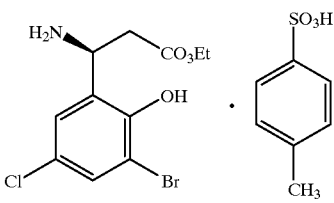

A solution of crude ester, prepared in Step 2 (~111 g), in ethanol (1500 mL) was charged under argon atmosphere to a 3-L 3-neck round bottom flask fitted with a mechanical stirrer. The reaction mixture was cooled to 0° C. and lead tetraacetate (88.67 g, 0.2 mol) was added in one portion. The reaction mixture was stirred for 3 hours at 0° C. and then 15% aqueous NaOH (150 mL) was added to the reaction mixture below 50° C. Methanol was removed under reduced pressure on rotavap. Another 150 mL of 15% aqueous NaOH was added and the reaction mixture was extracted with ethyl acetate (3×300 mL) and washed with DI water (2×100 mL) and brine (2×100 mL) and dried over anhydrous MgSO$_4$ (30 g). It was then filtered over celite and concentrated under reduced pressure to give the desired product (103 g) as a red oil.

Step 4

Preparation of

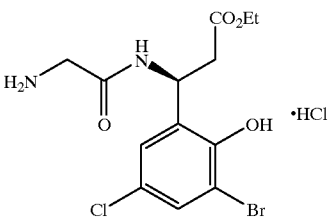

The above compound was prepared according to the procedure employed for Example I, Step 4 and Step 5 by substituting an equivalent amount of the product from Step 3 in Example I Step 4. MS and $^1$H NMR were consistent with the desired structure.

EXAMPLE K

Chiral Separation Methodology

Step 1

Preparation of

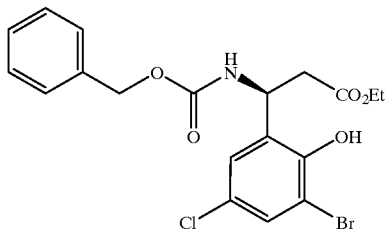

To the product of Example B, Step 3, (50.0 g, 139.2 mmol) and NaHCO$_3$ (33.5 g, 398.3 mmol) was added CH$_2$Cl$_2$ (500 mL) and water (335 mL). The mixture was stirred at room temperature for 10 minutes. A solution of benzyl chloroformate (38.0 g, 222.8 mmol) in CH$_2$Cl$_2$ (380 mL) was added over 20 minutes with rapid stirring. After 50 minutes, the reaction mixture was poured into a separatory funnel and the organic layer collected. The aqueous phase was washed with CH$_2$Cl$_2$ (170 mL). The combined organic layers were dried (MgSO$_4$) and concentrated in vacuo. The resulting gummy solid was triturated with hexane and collected by filtration. The tan solid was dried in vacuo to give the desired racemic product (61.2 g, 96% yield). This material was subjected to reverse phase HPLC using a chiral column to give each pure enantiomer. The column employed was a Whelk-O (R,R), 10 micron particle size using a 90:10 heptane: ethanol mobile phase. Optical purity was determined to be >98% using analytical hplc using similar column and solvent conditions. $^1$H NMR was consistent with the proposed structure.

Step 2

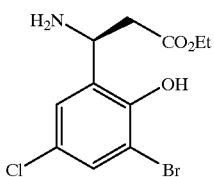

To a solution of the compound obtained in Step 1 (48.5 g, 106.2 mmol) in CH$_2$Cl$_2$ (450 mL) was added trimethylsilyl iodide (25.5 g, 127.4 mmol) in CH$_2$Cl$_2$ (100 mL) via cannula. The orange solution was stirred at room temperature for 1 hour. Methanol (20.6 mL, 509.7 mmol) was added dropwise and the solution stirred for 15 minutes. The reaction solution was concentrated in vacuo to give an orange oil. The residue was dissolved in methyl t-butyl ether (500 mL) and extracted with 1 N HCl (318 mL) and water (1×200 mL, 1×100 mL). The aqueous extracts were back washed with MTBE (100 mL). To the aqueous solution was added solid NaHCO$_3$ (40.1 g, 478 mmol) in small portions. The basified aqueous mixture was extracted with MTBE (1×1L, 2×200 mL). The combined organic solution was washed with brine and concentrated in vacuo to give the desired product (23.3 g, 68% yield). $^1$H NMR was consistent with the proposed structure.

Step 3

Preparation of

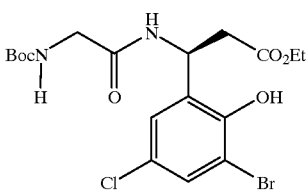

To a solution of the product from Step 2 (23.3 g, 72.1 mmol) in DMF (200 mL) was added N-t-Boc-glycine N-hydroxysuccinimide ester (17.9 g, 65.9 mmol). The reaction mixture was stirred at room temperature for 20 hours. The mixture was poured into ethyl acetate (1.2 L) and washed with 1M HCl (2×250 mL), saturated aqueous NaHCO$_3$ solution (2×250 mL) and brine (2×250 mL). The solution was dried (MgSO$_4$) and concentrated to give the desired product (32.0 g, 100% yield).

Anal. calcd for C$_{18}$H$_{24}$BrClN$_2$O$_6$: C, 45.06; H, 5.04; N, 5.84. Found: C, 45.17; H, 5.14; N, 6.12.

$^1$H NMR was consistent with the desired structure.

Step 4

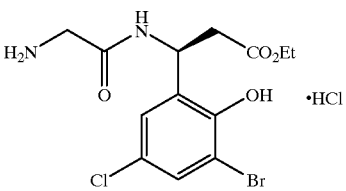

To a solution of the product of Step 3 (31.9 g, 66.5 mmol), in absolute ethanol (205 mL) was added an ethanolic HCl solution (111 mL of a 3M solution, 332.4 mmol). The reaction solution was heated at 58° C. for 30 minutes. The solution was cooled and concentrated in vacuo. The residue was dissolved in ethyl acetate (250 mL) and stirred at 0° C. for 2 hours. A white precipitate was collected by filtration and washed with cold ethyl acetate. The solid was dried in vacuo to give the desired product (23.5 g, 85% yield).

Anal. calcd for C$_{13}$H$_{16}$BrClN$_2$O$_4$+1.0 HCl: C, 37.53; H, 4.12; N, 6.73. Found: C, 37.29; H, 4.06; N, 6.68.

$^1$H NMR was consistent with the desired structure.

EXAMPLE L

Preparation of

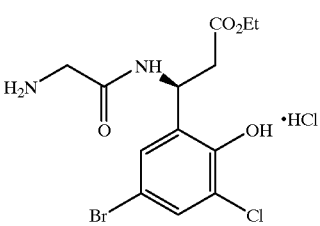

Step 1

Preparation of

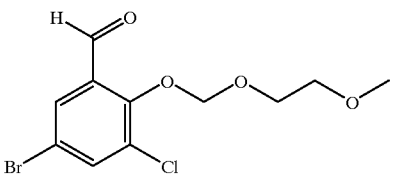

Potassium carbonate (powder, oven dried at 100° C. under vacuum, 22.1 g, 0.16 moles) was added to a solution of 3-chloro-5-bromosalicylaldehyde (35.0 g, 0.15 moles) in DMF (175 ml) at room temperature to give a bright yellow slurry. MEMCl (neat, 25.0 g, 0.2 moles) was then added while maintaining the bath temperature at 20° C. The mixture was then stirred at 22° C. for 6 hours and was poured into DI water (1200 mL) to precipitate the product. The slurry was filtered on a pressure filter and the cake was washed with DI water (2×400 mL) and was dried under $N_2$/vacuum to afford the product (46.0 g, 95% yield) as an off white solid. $^1$H NMR (CDCl$_3$, TMS) 3.35 (s, 3H), 3.54 to 3.56 (m, 2H), 3.91 to 3.93 (m, 2H), 5.30 (s, 2H), 7.77 (d, 1H), 7.85 (d, 1H), 10.30 (s, 1H); $^{13}$C NMR (CDCl$_3$, TMS) (ppm):59.05, 70.11, 71.49, 99.50, 117.93, 129.69, 129.78, 132.37, 138.14, 155.12, 188.22. DSC: 48.24° C. (endo 90.51 J/g); Microanalytical: calcd for $C_{11}H_{12}BrClO_4$: C: 40.82%; H: 3.74%; Cl: 10.95%; Br: 24.69%; found: C: 40.64%; H:3.48%; Cl: 10.99%; Br, 24.67%.

Step 2

Preparation of

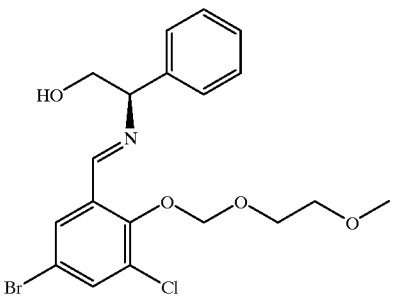

The product from Step 1 (32.35 g., 0.1 mol) was charged in a 500 ml 3N round bottom flask fitted with a mechanical stirrer, followed by addition of THF (160 ml) and (S)-phenylglycinol (13.71 g, 0.1 mol). After 30 minutes at 220° C., MgSO$_4$ (20 g.) was added. The mixture was stirred for 1 hour at 22° C. and filtered on a coarse fritted filter. The filtrate was concentrated under reduce pressure to afford a pale yellow oil (48.0 g) containing the desired imine. No further purification was performed and the crude product was used directly in the next reaction step.

Microanalytical: calcd for $C_{19}H_{21}BrClNO_4$: C: 51.54%; H: 4.78%; N: 3.16%; Br: 18.04%; Cl: 8.00%; found: C: 51.52%; H: 5.02%; N: 2.82%; Br: 16.31%; Cl:7.61%.

Step 3

Preparation of

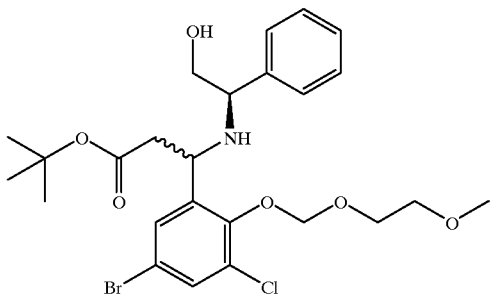

In a 5L 3N round bottom flask fitted with a mechanical stirrer, reagent from Example I, Step 1, (332 g, 0.8 mol) was taken up in NMP (660 mL) under nitrogen. The solution was then cooled to −10° C. A solution of imine produced in Step 2, in NMP (320 ml) was prepared under nitrogen and then added over 30 minutes to the above reaction mixture while the temperature was maintained at −5° C. The mixture was stirred for an additional hour after the addition was complete and cooled to −100° C. A mixture of concentrated HCl/saturated solution of NH$_4$Cl (30 mL/720 mL) was added over 10 minutes. MTBE (760 ml) was added and the mixture was stirred for 1 hour at 23° C. Stirring was stopped and the layers were separated. The aqueous layer was extracted with MTBE (320 ml). The two organic layers were combined, washed successively with a saturated solution of NH$_4$Cl (320 ml), DI water (320 ml) and brine (320 ml). The solution was dried with MgSO$_4$ (60 g), filtered and concentrated to afford a yellow oil (228 g) containing the desired product as a single diastereoisomer. DSC: 227.54° C. (endo. 61.63 J/g); Microanalytical: calcd for $C_{25}H_{33}BrClNO_6$: C: 53.72%; H: 5.95%; N: 2.50%; Br: 14.29%; Cl: 6.33%; found: C: 53.80%; H: 6.45%; N: 2.23%; Br: 12.85%; Cl:6.12%.

Step 4

Preparation of

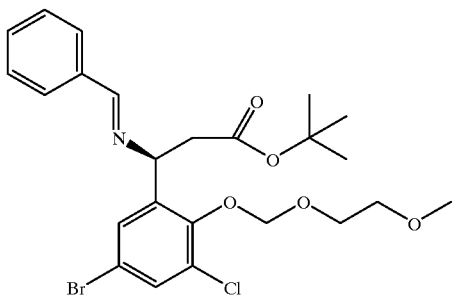

A solution of crude ester produced in Step 3 (~111 g) in ethanol (1500 mL) was charged under nitrogen atmosphere to a 3L 3N round bottom flask fitted with a mechanical stirrer. The reaction mixture was cooled to 0° C. and lead tetraacetate (88.67 g, 0.2 mol) was added in one portion. The reaction mixture was stirred for 3 hours at 0° C. and then 15% aqueous NaOH (150 mL) was added to the reaction mixture below 5° C. The ethanol was removed under reduced pressure on rotavap. Another 600 mL of 15% aqueous NaOH was added and the reaction mixture was extracted with ethyl acetate (2×300 mL), MTBE (2×200 mL) and ethyl acetate (2×200 mL). The organic layers were combined and washed with DI water (2×200 mL) and brine (2×100 mL) and dried over anhydrous MgSO₄ (30 g). The solution was then filtered over celite and concentrated under reduced pressure to give the product as an orange oil (96 g) that was used in the next step without further purification. DSC: 233.60° C. (endo. 67.85 J/g); Microanalytical: calcd for $C_{24}H_{29}BrClNO_5$: C: 54.71%; H: 5.54%; N: 2.65%; Br: 15.16%; Cl: 6.72%; found: C: 52.12%; H: 5.40%; N: 2.47%; Br: 14.77%; Cl:6.48%.

Step 5

Preparation of

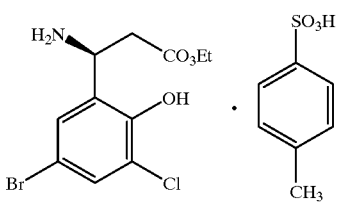

The crude product from Step 4 (~94 g) was taken up in absolute ethanol (180 mL) and para toluenesulfonic acid monohydrate (50.0 g, 0.26 mol) was added. The reaction mixture was then heated to reflux for 8 hours after which the solvent was removed under reduced pressure. The residual solid was taken up in THF (100 mL) and the THF was then stripped off under reduced pressure. The residue was dissolved in ethyl acetate (500 mL) and cooled to ~50° C. The solid was filtered and washed with heptane (2×50 mL) to give a white solid. The solid was then air dried to give the desired product as a white solid (38 g) as a single isomer. ¹H NMR (DMSO, TMS) (ppm) 1.12 (t, 3H), 2.29 (s, 3H), 3.0 (m, 2H), 4.05 (q, 2H), 4.88 (t, 1H), 7.11 (d, 2H), 7.48 (d, 2H), 7.55 (d, 1H), 7.68 (1H, d), 8.35 (br. s, 3H); ¹³C NMR (DMSO, TMS) (ppm):13.82, 20.75, 37.13, 45.59, 60.59, 110.63, 122.47, 125.44, 127.87, 128.06, 129.51, 131.95, 137.77, 145.33, 150.14, 168.98; DSC:69.86° C. (end., 406.5 J/g), 165.72° C. (end. 62.27 J/g), 211.24° C. (exo. 20.56 J/g) $[\alpha]^D_{25}$=+4.2° (c=0.960, MeOH); IR (MIR) (cm⁻¹) 2922, 1726, 1621, 1591, 1494, 1471, 1413, 1376, 1324, 1286, 1237, 1207; Microanalytical: calcd for $C_{18}H_{21}BrClNO_6S$: C: 43.69%; H:4.27%; N: 2.83%; Br: 16.15%, Cl: 7.16%, S: 6.48%; found: C: 43.40%; H:4.24%; N: 2.73%; Br: 16.40%, Cl: 7.20%, S: 6.54%.

Step 6

Preparation of

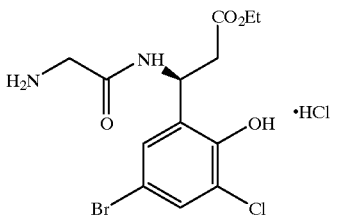

The above compound was prepared according to the procedures outlined in Example I, Step 4 and Step 5 where an equivalent quantity of the intermediate prepared in Step 5 as the free base is substituted fin Example I, Step 4.

MS and ¹H NMR were consistent with the desired structure.

EXAMPLE M

Preparation of

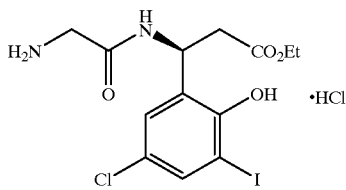

Step 1

Preparation of 3-Iodo-5-chlorosalicylaldehyde

N-Iodosuccinimide (144.0 g, 0.641 mole) was added to a solution of 5-chlorosalicylaldehyde (100 g, 0.638 mole) in dimethylformamide (400 mL). The reaction mixture was stirred for 2 days at room temperature. Additional N-iodosuccinimide (20.0 g) was added and stirring was continued for additional 2 days. The reaction mixture was diluted with ethyl acetate (1 L), washed with hydrochloric acid (300 mL, 0.1 N), water (300 mL), sodium thiosulfate (5%, 300 mL), brine (300 mL), dried (MgSO₄) and was concentrated to dryness to afford the desired aldehyde as a pale yellow solid (162 g, 90% yield).

MS and ¹H NMR were consistent with the desired structure.

Step 2

Preparation of 2-O-(MEM)-3-iodo-5-chlorosalicylaldehyde

Potassium carbonate (41.4 g, 0.30 mole) was added to a solution of 3-iodo-5-chlorosalicylaldehyde (84.74 g, 0.30 mole) in DMF (200 mL) at 20° C. This resulted in a yellow slurry and MEM-Cl (38.2 g, 0.305 mole) was added maintaining the reaction temperature. After 2 hours, additional MEM-Cl (1.5 g) was added. After stirring for 1 hour, the reaction mixture was poured into an ice-water mixture and was stirred. The precipitate formed, was filtered, and was dried in vacuo to afford the desired protected aldehyde. Yield: 95 g (85%).

MS and ¹H NMR were consistent with the desired structure.

Step 3

Preparation of

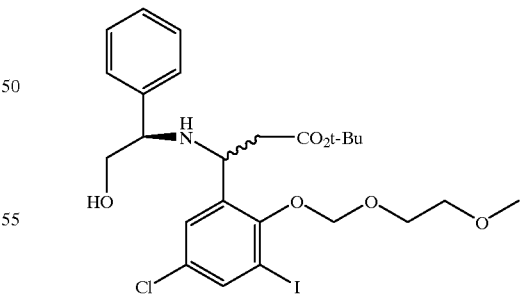

(S)-Phenyl glycinol (15.37 g, 0.112 mole) was added to a solution of 2-O-(MEM)-3-iodo-5-chlorosalicylaldehyde (41.5 g, 0.112 mole) in THF (200 mL) at room temperature. After 1 hour of stirring MgSO₄ (16 g) was added and the stirring was continued for 2 hours. The reaction mixture was filtered and the filtrate was concentrated and was dried in vacuo for 2 hours to obtain the desired intermediate imine. A 2-neck round bottomed flask was charged with the Reformatsky reagent from Example I, Step 1, (81.8 g, 0.2464 mole) and N-methylpyrrolidone (300 mL) and was stirred at −10° C. A solution of the imine in N-methylpyrrolidone (100 mL) was slowly added maintaining the temperature at −10° C. The mixture was maintained at this temperature for 2 hours and for 1 hour at −5° C. After cooling the reaction mixture to −10° C., a solution of concentrated HCl in saturated ammonium chloride (16 ml/200 mL) was added. Ethyl ether (500 mL) was added and was stirred for 2 hours at room temperature. The ether layer was separated, and the aqueous layer was further extracted with ether (300 mL). The combined ether layers were washed with saturated ammonium chloride (200 mL), water (200 mL), brine (200 mL), dried (MgSO$_4$) and concentrated to afford an oil (61.0 g, 90% yield). $^1$H NMR indicated that the desired structure was substantially one diastereomer and MS was consistent with the desired structure.

Step 4
Preparation of

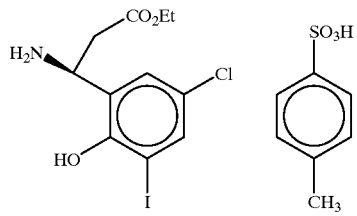

A solution of the crude ester produced in Step 3 (48.85 g, 80.61 mmol) was dissolved in ethanol (500 mL) and was cooled to 0° C. Lead tetraacetate (35.71 g, 80.61 mmol) was added. After 3 hours, 15% solution of NaOH (73 mL) was added to the reaction mixture. Most of the ethanol was removed under reduced pressure. To the residue was added a 15% solution of NaOH (200 mL) and which was then extracted with ether (400 mL). The ether layer was washed with water (100 mL), brine (100 mL), dried and was concentrated to afford an orange oil. The oil was dissolved in ethanol (100 mL) and para-toluenesulfonic acid (19.9 g) was added. The solution was heated at reflux for 8 hours and was concentrated under reduced pressure. The residue was diluted with THF (60 mL) and was heated at reflux and was cooled. The precipitate was filtered, washed with hexane/THF (300 mL, 1:1) and dried to afford the desired product.

MS and $^1$H NMR were consistent with the desired structure.

Step 5

S-Ethyl 3-(N-BOC-gly)-amino-3-(S)-(5-chloro-2-hydroxy-3-iodo)phenyl propionate

To a mixture of BOC-gly-OSu (9.4 g, 34.51 mmol), ethyl 3-(S)-amino-3-(5-chloro-2-hydroxy-3-iodo) propionate PTSA salt (17.0 g, 31.38 mmol) in DMF (200 mL) was added triethylamine (4.8 mL). The reaction mixture was stirred for 18 hours at room temperature. The DMF was removed in vacuo and the residue was partitioned between ethyl acetate (600 mL) and diluted hydrochloric acid (100 mL). The organic layer was washed with sodium bicarbonate (200 mL), brine (200 mL), dried (MgSO$_4$) and was concentrated to afford of the desired product as a solid (14.2 g, 86% yield).

MS and $^1$H NMR were consistent with the desired structure.

Step 6

S-Ethyl 3-(N-gly)-amino-3-(5-chloro-2-hydroxy-3-iodo)phenyl propionate hydrochloride Dioxane/HCl (4N, 70 mL) was added to ethyl 3-(S)-(N-BOC-gly)-amino-3-(5-chloro-2-hydroxy-3-iodo)phenyl propionate (37.20 g, 70.62 mmol) at 0° C. and was stirred at room temperature for 3 hours. The reaction mixture was concentrated, and concentrated once more after addition of toluene (100 mL). The residue obtained was suspended in ether, was filtered and dried to afford the desired product as a crystalline powder (32.0 g, 98% yield).

MS and $^1$H NMR were consistent with the desired structure.

EXAMPLE N

Preparation of

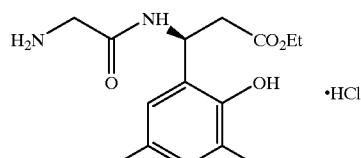

Step 1
Preparation of

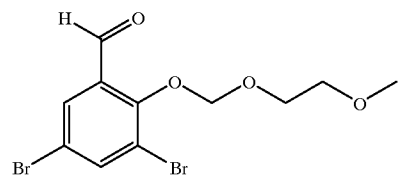

The above compound was prepared according to Example I, Step 2A, substituting an equivalent quantity of 2-hydroxy-3,5-dibromobenzaldehyde for 3,5-dichlorosalicylaldehyde. Yield 88%; Pale yellow solid; m. p. 46–47° C.; R$_f$=0.6 (EtOAc/Hexane 1:1 v/v); $^1$H-NMR (CDCl$_3$) d 3.37 (s, 3H), 3.56 (m, 2H), 3.92 (m, 2H), 5.29 (s, 2H), 7.91 (d, 1H, J=2.4 Hz), 7.94 (d, 1H, J=2.4 Hz), 10.27 (s, 1H); FAB-MS m/z 367 (M$^+$).

HR-MS calculated for C$_{11}$H$_{12}$Br$_2$O$_4$, 367.9083; found: 367.9077.

MS and $^1$H NMR were consistent with the desired structure.

Step 2

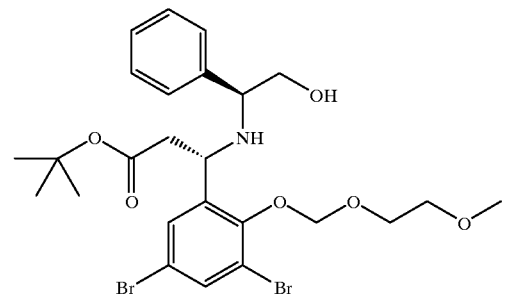

The above compound was prepared using the procedure of Example I, Step 2B and Step 2C, substituting an equivalent quantity of the compound of Step 1 in Example I, Step 2B.

Yield 90%; Yellow solid; m. p. 57–59° C.; $R_f$=0.46 (EtOAc/Hexane 1:1 v/v); $^1$H-NMR (CDCl$_3$) d 1.45 (s, 9H); 2.1 (br, 1H, exchangeable), 2.51 (d, 1H, $J_1$=9.9 Hz, $J_2$=15.3 Hz), 2.66 (d, 1H, $J_1$=4.2 Hz, $J_2$=15.3 Hz), 3.02 (br, 1H, exchangeable), 3.39 (s, 3H), 3.58–3.62 (m, 4H), 3.81 (m, 1H), 3.93 (m, 2H), 4.63 (dd, 1H, J=4.2 Hz), 5.15 (s, 2H), 7.17–7.25 (m, 6H), 7.49 (d, 1H); FAB-MS m/z 602 (M+H).

HR-MS calculated for $C_{25}H_{34}NBr_2O_6$; 602.0753; found: 602.0743.

MS and $^1$H NMR were consistent with the desired structure.

Step 3

Preparation of

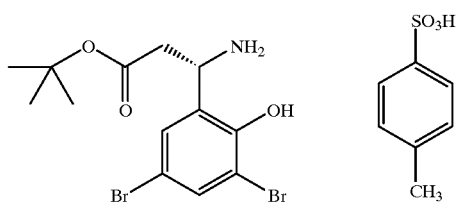

The above compound (p-toluenesulfonate salt) was prepared according to Example I, Step 3 by substituting an equivalent quantity of the product prepared in Step 2 in Example I, Step 3A. Yield 62%; white solid; $^1$H-NMR (DMSO-d$_6$) d 1.09 (t, 3H, J=7.2 Hz), 2.27 (s, 3H), 2.97(dd, 2H, $J_1$=3.0 Hz, $J_2$=7.2 Hz), 4.02 (q, 2H, J=7.2 Hz), 4.87 (t, 1H, J=7.2 Hz), 7.08 (d, 2H, J=4.8 Hz), 7.45 (m, 3H), 7.57 (d, 1H, J=2.4 Hz), 8.2 (br,3H); FAB-MS m/z 365 (M+H).

HR-MS calculated for $C_{11}H_{14}NBr_2O_3$, 365.9340; found: 365.9311.

MS and $^1$H NMR were consistent with the desired structure.

Step 4

Prepaaration of

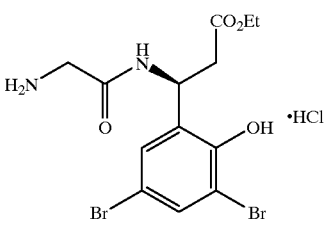

The above compound was prepared using the procedure of Example I, Step 4 substituting the compound prepared in Step 3. The resulting BOC protected intermediate, was converted to the desired compound using the procedure of Example I, Step 5.

MS and $^1$H NMR were consistent with the desired structure.

EXAMPLE P

Preparation of

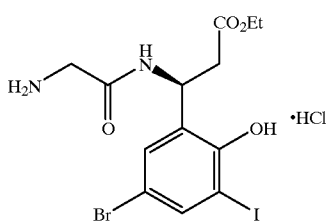

The above compound is prepared according to the procedure of Example I by substituting an equivalent amount of 3-iodo-5-bromosalicylaldehyde prepared in Example F, Step 1 for 3,5-dichlorosalicylaldehyde in Example I, Step 2A.

EXAMPLE Q

Preparation of

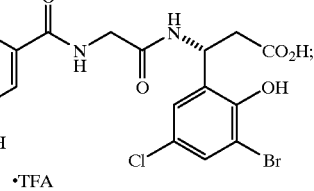

Step 1

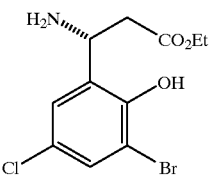

To a solution of the (R)-(CBZ)-β-amino ester from Example K, Step 1 (55.3 g, 121.0 mmol) in CH$_2$Cl$_2$ (500 mL) was added trimethylsilyl iodide (30.5 g, 152.0 mmol) in CH$_2$Cl$_2$ (100 mL) via cannula. The reaction solution was stirred at room temperature for 1.5 hours. Methanol (25.0 mL, 609.2 mmol) was added dropwise and the solution stirred for 15 minutes. The reaction solution was concentrated in vacuo. The residue was dissolved in MTBE (550 mL) and extracted with 1M HCl (340 mL) and water (1×200 mL, 1×150 mL). The aqueous extracts were back washed with MTBE (150 mL). To the aqueous solution was added solid NaHCO$_3$ (43.0 g, 512 mmol) in small portions. The basified aqueous mixture was extracted with MTBE (1×1L, 2×250 mL). The combined organic solution was washed with brine and concentrated in vacuo to give the desired product (30.3 g, 76% yield). 1H NMR was consistent with the proposed structure. Anal. Calcd. For $C_{11}H_{13}BrClNO_3$+ 0.5H$_2$O: C, 39.84; H, 4.26; N, 4.22; Found: C, 39.49; H, 3.89; N, 4.13.

Step 2

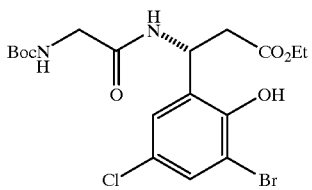

To a solution of the amine obtained in Step 1 (29.3 g, 90.7 mmol) in DMF (250 mL) was added N-t-Boc-glycine N-hydroxysuccinimide ester (24.7 g, 90.7 mmol). The reaction mixture was stirred at room temperature for 20 hours. The mixture was poured into ethyl acetate (1.2 L) and washed with 1M HCl (2×250 mL), saturated aqueous NaHCO$_3$ solution (2×250 mL) and brine (2×250 mL). The solution was dried (MgSO$_4$) and concentrated in vacuo to give the desired product (43.8 g, 100% yield). 1H NMR was consistent with the proposed structure.

Step 3

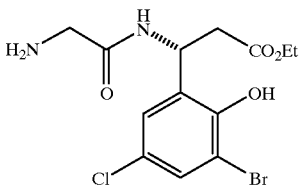

To a solution of the product from Step 2 (43.5 g, 90.7 mmol) in absolute ethanol (300 mL) was added an ethanolic HCl solution (105 mL of a 4.3M solution, 453.5 mmol). The reaction solution was kept at room temperature for 1 hour. The solution was cooled and concentrated in vacuo. The residue was dissolved in ethyl acetate (300 mL) and stirred at 0° C. for 2 hours. A white precipitate was collected by filtration and washed with cold ethyl acetate. The solid was dried in vacuo to give the desired product (30.4 g, 81% yield). 1H NMR was consistent with the proposed structure.

Step 4

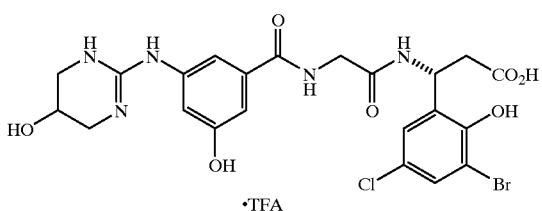

To a solution of the product from Example H (3.0 g, 10.3 mmol) in DMA (10 mL) at −8° C. was added IBCF (1.5 mL, 11.4 mmol) and NMM (1.3 mL, 11.4 mmol). The reaction solution was warmed to 8° C. over 30 minutes. The solution was cooled to −5° C. and a solution of the product from Step 3 (4.3 g, 10.3 mmol) in DMA (18 mL) was added followed by NMM (1.3 mL, 11.4 mmol). The reaction mixture was warmed to room temperature and stirred overnight. The mixture was filtered and the filtrate was concentrated in vacua. The residue was dissolved in 2.5N NaOH (30 mL) and water (30 mL). The reaction solution was kept at room temperature for 1.5 hours. The pH was adjusted to about 5 and the product was purified by reverse phase HPLC (95:5 H$_2$O/TFA:MeCN to 80:20 H$_2$O/TFA:MeCN) to give the desired product (1.8 g, 22%). Anal. Calcd for C$_{22}$H$_{23}$BrClN$_5$O$_7$+1.6 TFA: C, 39.45; H, 3.23; N, 9.13; Found: C, 39.36; H, 3.32; N, 9.52.

1H NMR was consistent with the proposed structure.

EXAMPLE R

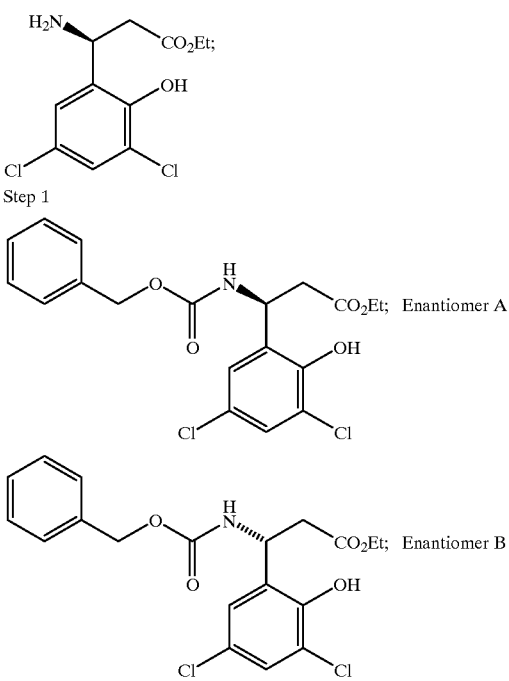

To the product from Example A, Step 2 (50.0 g, 158.9 mmol) and NaHCO$_3$ (38.2 g, 454.5 mmol) was added CH$_2$Cl$_2$ (500 mL) and water (380 mL). The mixture was stirred at room temperature for 10 minutes with vigorous gas evolution. A solution of benzyl chloroformate (43.4 g, 222.8 mmol) in CH$_2$Cl$_2$(435 mL) was added over 20 minutes with rapid stirring. After 40 minutes, the reaction mixture was poured into a separatory funnel and the organic solution collected. The aqueous phase was washed with CH$_2$Cl$_2$(170 mL). The combined organic solution was dried (MgSO$_4$) and concentrated in vacuo. The resulting gummy solid was triturated with hexane and collected by filtration. The tan solid was dried in vacuo to give the desired racemic product (62.9 g, 96%). This material was subjected to reverse phase HPLC using a chiral column to give each pure enantiomer, A and B. The column employed was a Whelk-O (R,R), 10 micron particle size using a 90:10 heptane:ethanol mobile phase. Optical purity was determined to be >98% using analytical hplc with similar solvent and conditions. $^1$H NMR spectrum was consistent with proposed structure.

Step 2

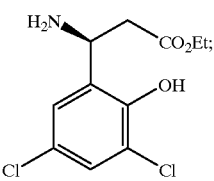

To a solution of Enantiomer A, Step 1 (57.9 g, 140.4 mmol) in CH$_2$Cl$_2$(600 mL) was added trimethylsilyl iodide (33.7 g, 168.5 mmol) in CH$_2$Cl$_2$(125 mL) via canula. The orange solution was stirred at room temperature for 1 hour. Methanol (27.3 mL, 674.1 mmol) was added dropwise and the solution stirred for 15 minutes. The reaction solution was concentrated in vacuo to give an orange oil. The residue was dissolved in methyl t-butyl ether (670 mL) and extracted with 1M HCl (420 mL) and water (1×230 mL, 1×130 mL). The aqueous extracts were back washed with MTBE (130 mL). To the aqueous solution was added solid NaHCO$_3$(52.9 g, 630 mmol) in small portions. The basified aqueous mixture was extracted with MTBE (1×1.2 L, 2×265 mmL). The combined organic solution was washed with brine and concentrated in vacuo to give the desired product, (28.6 g, 73%). $^1$H NMR spectrum was consistent with proposed structure.

EXAMPLE S

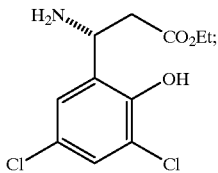

To a solution of the Enantiomer B, Step 1, Example R (38.5 g, 93.4 mmol) in CH$_2$Cl$_2$ (380 mL) was added trimethylsilyl iodide (25.0 g. 125.0 mmol) in CH$_2$Cl$_2$ (80 mL) via cannula. The orange solution was stirred at room temperature for 1.5 hours. Methanol (20.0 mL, 500.0 mmol) was added dropwise and the solution stirred for 20 minutes. The reaction solution was concentrated in vacuo to give an orange oil. The residue was dissolved in diethyl ether (450 mL) and extracted with 1 M HCl (320 mL) and water (1×200 mL, 1×100 mL). The aqueous extracts were back washed with diethyl ether (100 mL). To the aqueous solution was added solid NaHCO$_3$ (40.1 g, 478 mmol) in small portions. The basified aqueous mixture was extracted with diethyl ether (1×1.0 L, 2×200 mL). The combined organic solution was washed with brine and concentrated in vacuo to give the desired product, (20.8 g, 80%). Anal. calcd for C$_{11}$H$_{13}$Cl$_2$NO$_3$: C, 47.50; H, 4:71; N, 5.04; Found: C, 47.11; H, 4.66; N, 4.93.

EXAMPLE 1

(α) 3-bromo-5-chloro-2-hydroxy-β-[[2-[[[3-hydroxy-5-[(1,4,5,6-tetrahydro-5-hydroxypyrimidin-2-yl)amino]pheny]carbonyl]amino]-acetyl]amino] benzenepropanoic acid, trifluroacetate salt Preparation of

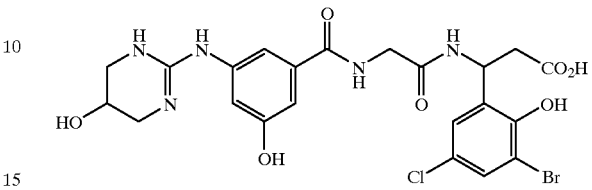

To the product of Example H (0.4 g, 0.0014 mole), the product of Example B (0.58 g, 0.0014 mole), triethylamine (0.142 g, 0.0014 mole), DMAP (17 mg), and anhydrous DMA (4 ml) was added EDCl (0.268 g, 0.0014 mole) at ice bath temperature. The reaction was stirred overnight at room temperature. The resulting ester intermediate was isolated by reverse phase preparatory HPLC. To this ester in H$_2$O (10 ml) and CH$_3$CN (5 ml) was added LiOH (580 mg, 0.0138 mole). After stirring at room temperature for 1 hour, the pH was lowered to 2 with TFA and the product was purified by reverse phase preparatory HPLC to yield (after lyophilization) the desired product as a white solid (230 mg).

MS and $^1$H NMR were consistent with the desired structure.

EXAMPLE 2

Preparation of

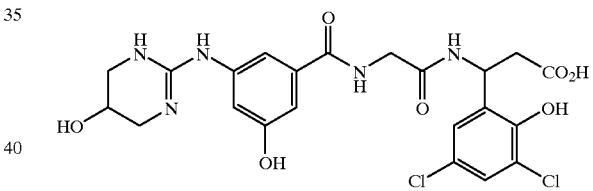

The above compound was prepared according to the methodology of Example 1, substituting an equivalent amount of the product from Example A for the product from Example B. The yield, after lyophilization was 320 mg of as a white solid.

MS and $^1$H NMR were consistent with the desired structure.

EXAMPLE 3

Preparation of

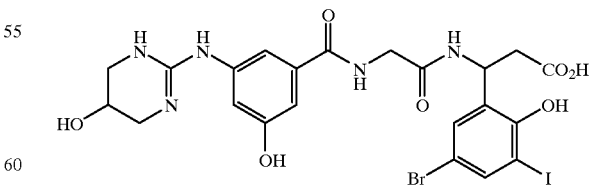

The above compound was prepared according to the methodology of Example 1, substituting an equivalent amount of the product from Example F for the product from Example B. The yield (after lyophilization) was 180 mg as a white solid.

MS and ¹H NMR were consistent with the desired structure.

EXAMPLE 4

Preparation of

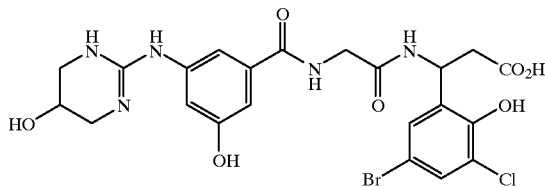

The above compound was prepared according to the methodology of Example 1, substituting an equivalent amount of the product of Example D for the product of Example B. The yield (after lyophilization) was 180 mg as a white solid.

MS and ¹H NMR were consistent with the desired structure.

EXAMPLE 5

Preparation of

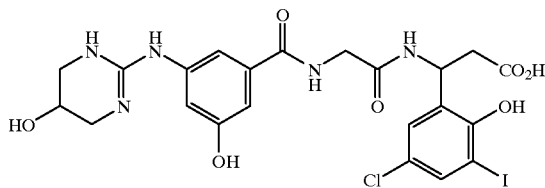

The above compound was prepared according to the methodology of Example 1, substituting an equivalent amount of the product from Example E for the product from Example B. The yield (after lyophilization) was 250 mg as a white solid.

MS and ¹H NMR were consistent with the desired structure.

EXAMPLE 6

Preparation of

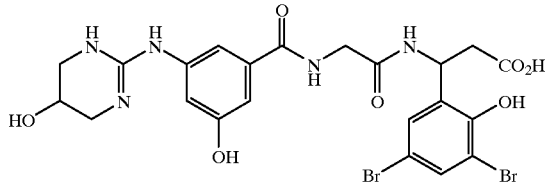

The above compound was prepared according to the methodology of Example 1 substituting an equivalent amount of the product from Example C for the product from Example B. The yield (after lyophilization) was 220 mg as a white solid.

MS and ¹H NMR were consistent with the desired product.

EXAMPLE 7

Preparation of

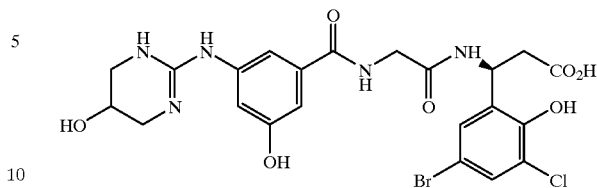

To the product from Example H (7.8 g, 0.027 mole) dissolved in anhydrous DMA (50 mL) in a flame dried flask under $N_2$ and at ice bath temperature was slowly added isobutylchloroformate (3.7 g, 0.027 mole) followed by N-methylmorpholine (2.73 g, 0.027 mole). The solution was stirred at ice bath temperature for 15 minutes. To the reaction mixture was then added the product from Example L (10.0 g, 0.024 mole) at ice bath temperature followed by N-methylmorpholine (2.43 g, 0.024 mole). The reaction was then stirred at room temperature overnight. The resulting ester intermediate was isolated by reverse phase prep HPLC. To the ester in $H_2O$ (60 mL) and $CH_3CN$ (30 mL) was added LiOH (10 g, 0.238 mole). The reaction mixture was stirred at room temperature for 1 hour. The pH was then lowered to 2 with TFA. The product was purified by reverse phase prep HPLC to yield (after lyophilization) the desired product as a white solid (9.7 g).

MS and ¹H NMR were consistent with the desired structure.

EXAMPLE 8

(S) 3,5-dichloro-2-hydroxy-β-[[2-[[[3-hydroxy-5-[(1,4,5,6-tetrahydro-5-hydroxypyrimidin-2-yl)amino]phenyl]carbonyl]amino]acetyl]amino]-benzenepropanoic acid, monohydrochloride monohydrate Preparation of

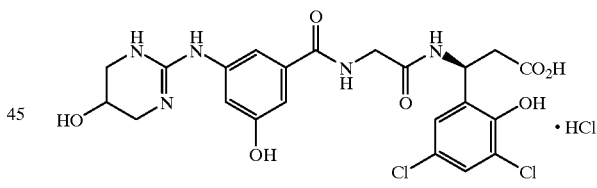

Step A

To the product from Example H (9.92 g, 0.0345 mole) dissolved in anhydrous DME (200 mL) is added N-methylmorpholine (4.0 mL, 0.0362 mole). The reaction mixture was cooled to −5° C. (salt-ice bath). Isobutyichloroformate, IBCF (4.48 mL, 4.713 g, 0.0345 mole) was added over one minute and the reaction mixture stirred at ice bath temperature for 12 minutes. To the reaction mixture was then added the product from Example I (11.15 g, 0.030 mole) at ice bath temperature followed by N-methylmorpholine (4.0 mL, 0.0362 mole). The reaction mixture was allowed to warm to room temperature and go to completion then concentrated under vacuum at 50° C. to give a dark residue. The residue was dissolved in acetonitrile: $H_2O$ (about 50 mL). The pH was made acidic by addition of a small amount of TFA. The residue was placed on a 10×500 cm C-18 (50 u particle size) column and the ester of the desired product isolated. (Solvent program: 100% H₂O+0.05% TFA to 30:70 H₂O+0.05% TFA: acetonitrile+0.05% TFA over 1 hour @ 100 mL/minute: the solvent program was initiated after the solvent front elutes). Preparatory RPHPLC purification resulted in a white solid (10.5 g) after lyophilization (50%).

MS and ¹H NMR were consistent with the desired structure.

Step B

The product produced in Step A (about 11 g) was dissolved in dioxane: water and the pH of the solution adjusted to approximately 11.5 (pH meter) by the addition of 2.5 N NaOH. The reaction mixture was stirred at room temperature. Periodically, the pH was re-adjusted to >11 by further addition of base. After 2–3 hours the conversion of ester to acid was deemed complete by RPHPLC. The pH of the reaction mixture was adjusted to about 6 and a viscous oil precipitated from solution. The oil was isolated by decantation and washed with hot water (200 mL). The resulting aqueous mixture was allowed to cool and the solid was collected by filtration to yield The above compound (2.6 g after lyophilization from HCl solution). The residue, which was a dark viscous oil was treated with hot water to give on cooling a tan powder (4.12 g after lyophilization from HCl solution).

MS and ¹H NMR were consistent with the desired structure.

EXAMPLE 9

(S) 3-bromo-5-chloro-2-hydroxy-β-[[2-[[[3-hydroxy-5-[(1,4,5,6-tetrahydro-5-hydroxypyrimidin-2-yl)amino]phenyl]carbonyl]amino]acetyl]amino]-benzenepropanoic acid, trifluoroacetate salt Step 1
Preparation of

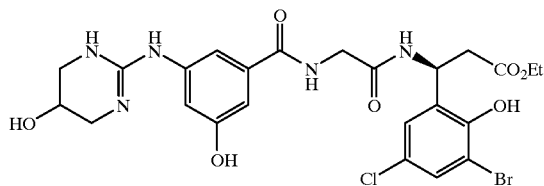

To a suspension of the product from Example J (1.0 g, 2.4 mmol), the product from Example H (0.75 g, 2.6 mmol) and 4-dimethylaminopyridine (40 mg) in N,N-dimethylacetamide (10 mL) was added triethylamine (0.24 g, 2.4 mmol). The mixture was stirred at room temperature for 15 minutes and 1-(3-dimethylaminopropyl)-3-ethylcarbodiimide hydrochloride (0.60 g, 3.1 mmol). The reaction mixture was stirred at room temperature overnight. The mixture was concentrated in vacuo and purified by reverse phase HPLC (starting gradient 90:10 H₂O/TFA:MeCN, retention time 22 minutes) to give the desired product, (1.6 g, 52% yield).

¹H NMR was consistent with the proposed structure.

Step 2

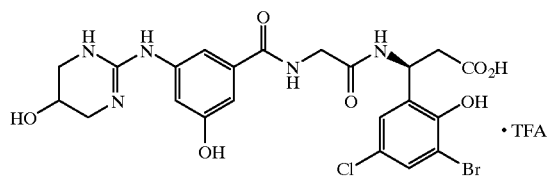

To a solution of the ester produced in Step 1 (800 mg, 1.2 mmol) in a 1:4 MeCN:H₂O solution (7 mL) was added lithium hydroxide (148 mg, 6.2 mmol). The reaction mixture was stirred at room temperature for 2 hours. TFA (0.71 mL, 9.2 mmol) was added and the mixture purified by reverse phase HPLC (starting gradient 95:5 H₂O/TFA:MeCN, retention time 24 minutes) to give the desired product (860 mg, 83% yield).

Anal. calcd for C₂₂H₂₃BrClN₅O₇+1.7 TFA: C, 39.18; H, 3.20; N, 8.99. Found: C, 39.11; H, 3.17; N, 9.07.

MS and ¹H NMR were consistent with the desired structure.

Step 3
Preparation of the hydrochloride salt

The product of Step 2 was dissolved in a suitable solvent (acetontrile: water) and the solution slowly passed through a Bio-Rad AG2 −8× (chloride form, 200–400 mesh, >5 equivalents) ion-exchange column. Lyophilization gives the desired product as an HCl salt.

EXAMPLE 10
Preparation of

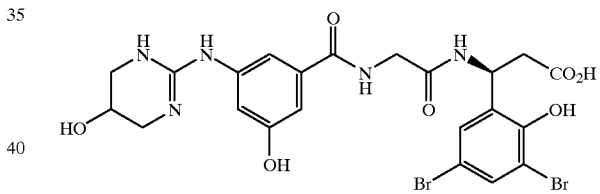

The above compound was prepared using the procedure of Example 8 substituting the product of Example N for the product of Example I in Example 8, Step A. The product was isolated by prep RPHPLC and lyophilized to give the desired product as a TFA salt.

MS and ¹H NMR were consistent with the desired structure.

EXAMPLE 11
Preparation of

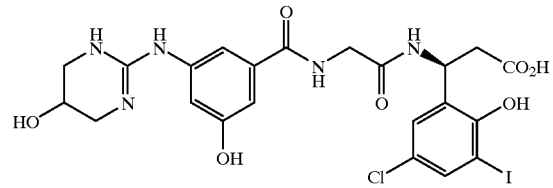

The above compound was prepared using essentially the procedures of Example 8 and substituting the product of Example M for the product of Example I in Example 8, Step A. The product was isolated by preparatory RPHPLC and lyophilized to give the desired product as a TFA salt.

MS and $^1$H NMR were consistent with the desired structure.

EXAMPLE 12

Preparation of

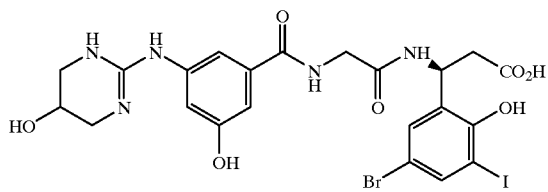

The above compound was prepared using the procedures of Example 8 and substituting the product of Example P for the product of Example I in Example 8, Step A. The product is isolated by prep RPHPLC and lyophilized to give the desired product as a TFA salt.

EXAMPLE 13

Preparation of

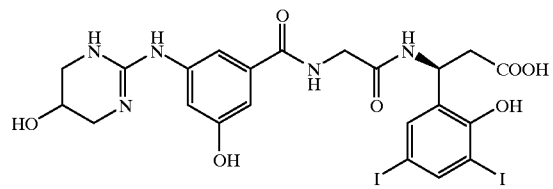

Preparation of 2-O-(MEM)-3,5-diiodosalicylaldehyde

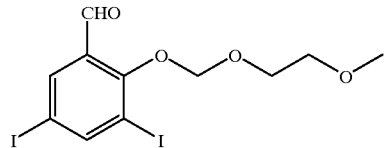

Potassium carbonate (18.5 g, 0.134 mole) was added to a solution of 3,5-diiodosalicylaldehyde (50.0 g, 0.134 mole) in DMF (150 mL) at 20° C. This resulted in a yellow slurry and MEM-Cl (15.8 mL, 0.134 mole) was added maintaining the reaction temperature. After 2 hours, additional MEM-Cl (1.5 g) was added. After stirring for a further 1hour, the reaction mixture was poured into ice-water and stirred. The precipitate formed, was filtered, and dried in vacuo to afford the desired protected aldehyde (61 g, 99% yield). $^1$H NMR was consistent with the desired product.

Step 2

Preparation of

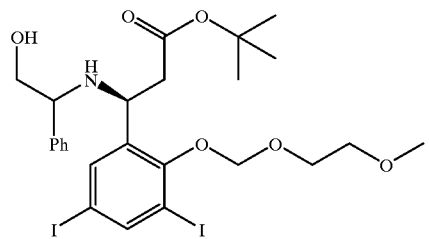

(S)-phenyl glycinol (17.9 g, 0.13 mole) was added to a solution of 2-O-(MEM)-3,5-diiodosalicylaldehyde (41.5 g, 0.112 mole) in THF (150 mL) at room temperature. After 1 hour of stirring MgSO$_4$ (20.7 g) was added and the stirring was continued for 2 hours. The reaction mixture was filtered and the filtrate was concentrated and dried in vacuo for 2 hours. A 2-neck round bottomed flask was charged with the Reformatsky reagent (96 g, 0.289 mole) and N-methylpyrrolidone (250 mL) and was stirred at −10° C. A solution of the imine in N-methylpyrrolidone (100 mL) was slowly added maintaining the temperature at −10° C. The mixture was maintained at this temperature for 2 hours and for 1 hour at −5° C. After cooling the reaction mixture to −10° C., a solution of concentrated HCl in saturated ammonium chloride (16 ml/200 mL) was added. Ethyl ether (500 mL) was added and the mixture was stirred for 2 hours at room temperature. The ether layer was separated, and the aqueous layer further extracted with ether (300 mL). The combined ether layers were washed with saturated ammonium chloride (200 mL), water (200 mL), brine (200 mL), dried (MgSO$_4$) and concentrated to afford an oil (90.0 g, 99% yield). NMR indicated desired product and one diastereomer.

Step 3

Preparation of

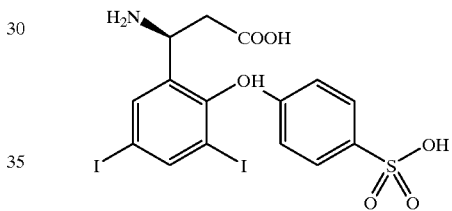

A solution of the crude ester from Step 2 (14.0 g, 20.1 mmol) was dissolved in ethanol (100 mL) and was cooled to 0° C. Lead tetra acetate (9.20 g, 20.75 mmol) was added in one lot. After 3 hours, 15% solution of NaOH (73 mL) was added to the reaction mixture. Most of the ethanol was removed under reduced pressure. The residue was added to a 15% solution of NaOH (200 mL) which was extracted with ether (400 mL). The ether layer was washed with water (100 mL), brine (100 mL), dried and concentrated to afford an orange oil. This was dissolved in ethanol (100 mL) and para-toluenesulfonic acid (6.08 g) was added. The solution was heated at reflux for 8 hours and was concentrated under reduced pressure. The residue was diluted with THF (60 mL), was heated at reflux and was cooled. Upon storage, no precipitate formed. The reaction mixture was concentrated and purified by preparative hpic to afford the amino acid as its PTSA salt. The solid obtained was dissolved in ethanol and was saturated with HCl gas. The reaction mixture was heated at reflux for 6 hours. The reaction mixture was concentrated to afford the PTSA salt of the desired amino acid (12.47 g).

Step 4

Preparation of Ethyl 3-(N-BOC-gly)-amino-3-(S)-(3,5-diiodo-2-hydroxyphenyl)propionate

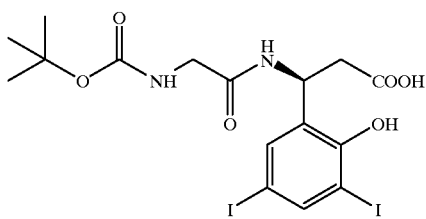

To a mixture of BOC-gly-OSu (7.48 g, 27.04 mmol), ethyl 3-(S)-amino-3-(3,5-diiodo-2-hydroxyphenyl)propionate PTSA salt (12.47 g, 27.04 mmol) in DMF (100 mL) was added triethylamine (3.8 mL). The reaction mixture was stirred for 18 hours at room temperature. The DMF was removed in vacuo and the residue partitioned between ethyl acetate (600 mL) and dilute hydrochloric acid (100 mL). The organic layer was washed with sodium bicarbonate (200 mL), brine (200 mL), dried (MgSO4) and concentrated to afford the desired product as a solid (17.0 g, 96% yield). $^1$H NMR was consistent with the desired product.

Step 5
Preparation of ethyl 3-(N-gly)-amino-3-(3,5-diiodo-2-hydroxyphenyl)propionate hydrochloride

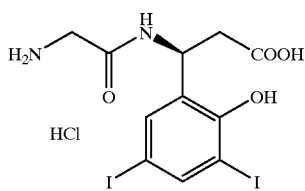

To dioxane/HCl (4N, 40 mL) was added ethyl 3-(N-BOC-gly)-amino-3-(S)-(3,5-diiodo-2-hydroxyphenyl)propionate (17.0 g, 25.97 mmol) at 0° C. and the reaction mixture was stirred at room temperature for 3 hours. The reaction mixture was concentrated, and concentrated once more after addition of toluene (100 mL). The residue obtained was dried to afford the desired product as a crystalline powder (8.0 g, 56% yield). $^1$H NMR is consistent with the desired product.

Step 6
A solution of m-(5-hydroxypyrimidino)hippuric acid (3.74 g, 12.98 mmol) in dimethylacetamide (25 mL) was heated until all the material had dissolved. This was then cooled to 0° C. and isobutylchloroformate (1.68 mL) was added in one portion followed by N-methylmorpholine (1.45 mL). After 10 minutes, ethyl 3-(N-gly)-amino-3-(3,5-diiodo-2-hydroxyphenyl)propionate hydrochloride (6.0 g, 10.82 mmol) was added in one portion followed by N-methylmorpholine (1.45 mL). The reaction mixture was stirred for 18 hours at room temperature. The reaction mixture was concentrated, the residue dissolved in tetrahydrofuran/water (1:1, 20 mL), and was chromatographed (reverse phase, 95:5 water acetonitrile over 60 minutes to 30:70 water: acetonitrile containing 0.1% TFA). The combined fractions were concentrated. The residue was dissolved in acetonitrile water and lithium hydroxide was added until basic. The solution was stirred for 2 hours. The reaction mixture was concentrated and was purified as above by hpic to afford the desired acid as the TFA salt. The TFA salt was converted to the corresponding hydrochloride salt by passing through an ion-exchange column followed by lyophilization. $^1$H NMR was consistent with the desired product.

What is claimed is:
1. A method for the preparation of a chiral β-amino ester of the formula

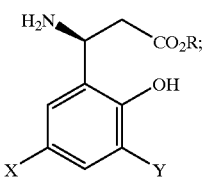

wherein R is lower alkyl; X and Y are the same or different halogens selected from the group consisting of Cl, Br and I; comprising protecting the amino group of a racemic amino acid of the formula

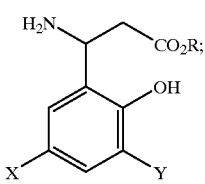

with a CBZ protecting group to produce a protected amino acid compound of the formula

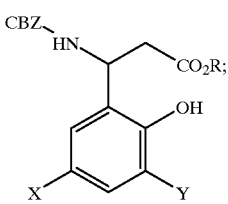

subjecting the protected amino acid compound so obtained to chiral chromatography to obtain a chiral protected amino acid of the formula

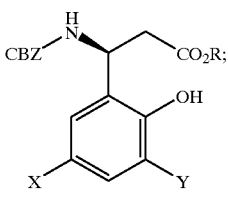

deprotecting the chiral protected amino acid so obtained by reacting with trimethylsilyl iodide in dichloromethane; and isolating the chiral β-amino ester of the formula

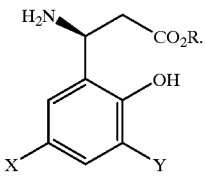

2. A method for the preparation of a chiral β-amino ester of the formula

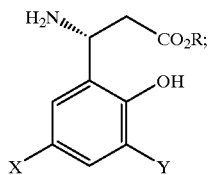

wherein R is lower alkyl; X and Y are the same or different Cl, Br or I; comprising protecting the amino group of a racemic amino acid of the formula

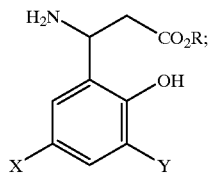

with a CBZ protecting group to produce a protected amino acid compound of the formula

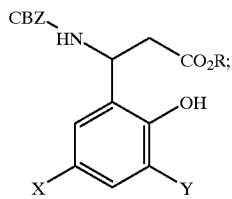

subjecting the protected amino acid compound so obtained to chiral chromatography to obtain a chiral protected amino acid of the formula

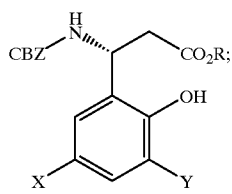

deprotecting the protected chiral amino acid so obtained by reacting with trimethylsilyl iodide in dichloromethane; and isolating the chiral β-amino ester of the formula

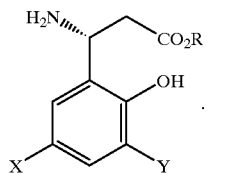

3. A method for the preparation of a chiral β-amino ester of the formula

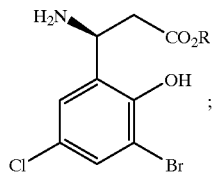

wherein R is lower alkyl; comprising protecting the amino group of a racemic amino acid of the formula

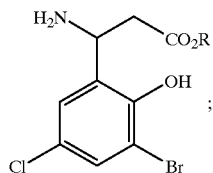

with a CBZ protecting group to produce amino acid compound of the formula

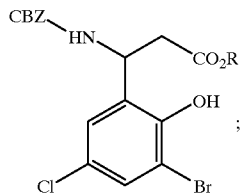

subjecting the protected amino acid compound so obtained to chiral chromatography to obtain a chiral protected amino acid of the formula

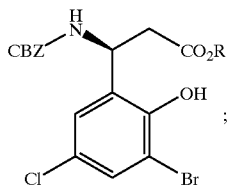

deprotecting the chiral protected amino acid so obtained by reacting with trimethylsilyl iodide in dichloromethane; and isolating the chiral β-amino ester or the formula

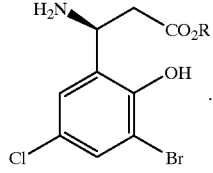

4. A method for the preparation of a chiral β-amino ester of the formula

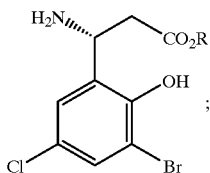

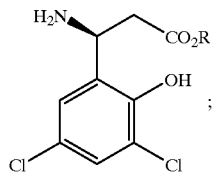

wherein R is lower alkyl; comprising protecting the amino group of a racemic amino acid of the formula

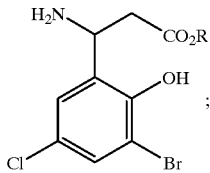

with a CBZ protecting group to produce a protected amino acid compound of the formula

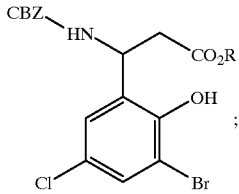

subjecting the protected amino acid compound so obtained to chiral chromatography to obtain a chiral protected amino acid of the formula

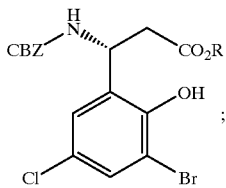

deprotecting the protected chiral amino acid so obtained by reacting with trimethylsilyl iodide in dichloromethane; and isolating the chiral β-amino ester of the formula

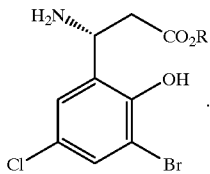

5. A method for the preparation of a chiral β-amino ester of the formula wherein R is lower alkyl; comprising protecting the amino group of a racemic amino acid of the formula

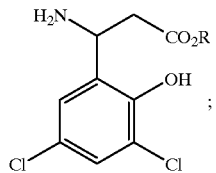

with a CBZ protecting group to produce a protected amino acid compound of the formula

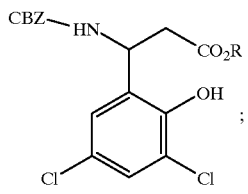

subjecting the protected amino acid compound so obtained to chiral chromatography to obtain a chiral protected amino acid of the formula

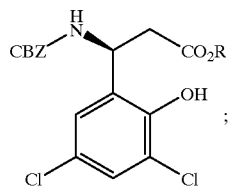

deprotecting the chiral protected amino acid so obtained by reacting with trimethylsilyl iodide in dichloromethane; and isolating the chiral β-amino ester or the formula

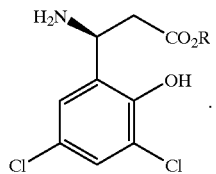

6. A method for the preparation of a chiral β-amino ester of the formula

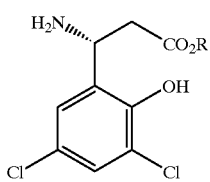

wherein R is lower alkyl; comprising protecting the amino group of a racemic amino acid of the formula

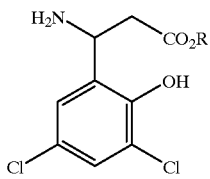

with a CBZ protecting group to produce a protected amino acid compound of the formula

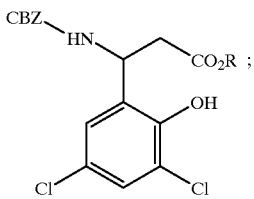

subjecting the protected amino acid compound so obtained to chiral chromatography to obtain a chiral protected amino acid of the formula

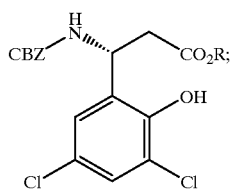

deprotecting the protected chiral amino acid so obtained by reacting with trimethylsilyl iodide in dichloromethane; and isolating the chiral β-amino ester of the formula

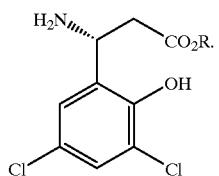

* * * * *